United States Patent [19]
Cox

[11] Patent Number: 5,257,974
[45] Date of Patent: Nov. 2, 1993

[54] PERFORMANCE ENHANCEMENT ADAPTOR FOR INTRAVASCULAR BALLOON CATHETER

[75] Inventor: James E. Cox, Plymouth, Minn.

[73] Assignee: SciMed Life Systems, Inc., Maple Grove, Minn.

[21] Appl. No.: 932,219

[22] Filed: Aug. 19, 1992

[51] Int. Cl.⁵ ............................................. A61M 25/10
[52] U.S. Cl. .................................... 604/96; 128/772; 606/194
[58] Field of Search ................... 604/96–103, 604/280, 165, 265; 606/191–194; 128/772

[56] References Cited

U.S. PATENT DOCUMENTS

| | | |
|---|---|---|
| 1,690,995 | 11/1928 | Pratt . |
| 4,540,404 | 9/1985 | Wolvek ................................ 604/96 |
| 4,723,549 | 2/1988 | Wholey et al. ..................... 128/344 |
| 4,877,030 | 10/1989 | Beck et al. ......................... 128/343 |
| 5,180,366 | 1/1993 | Woods ................................. 604/96 |
| 5,192,295 | 3/1993 | Danforth et al. ................... 606/194 |
| 5,195,989 | 3/1993 | Euteneuer ........................ 604/96 X |

FOREIGN PATENT DOCUMENTS

0461474A1 12/1991 European Pat. Off. .
1547328 6/1979 United Kingdom .

*Primary Examiner*—John D. Yasko
*Attorney, Agent, or Firm*—Nawrocki, Rooney & Sivertson

[57] ABSTRACT

An adaptor for use with balloons of intravascular balloon catheters commonly used for treating conditions of the vascular system includes a hollow member and an elongated positioning member, which is connected to the hollow member. The hollow member possesses characteristics not possessed by the balloon of the balloon catheter. With a balloon catheter positioned within a blood vessel, the adaptor is capable of longitudinal movement through the blood vessel, between the balloon catheter and a wall of the blood vessel, independent of the balloon catheter. The adaptor is manuevered adjacent to the balloon by manipulating the positioning member until a proximal end and a distal end of the adaptor is generally aligned with a proximal and distal end of the balloon, respectively. Inflation of the balloon secures the hollow member against the balloon in such a manner that the characteristics of the hollow member are imparted to the balloon.

59 Claims, 13 Drawing Sheets

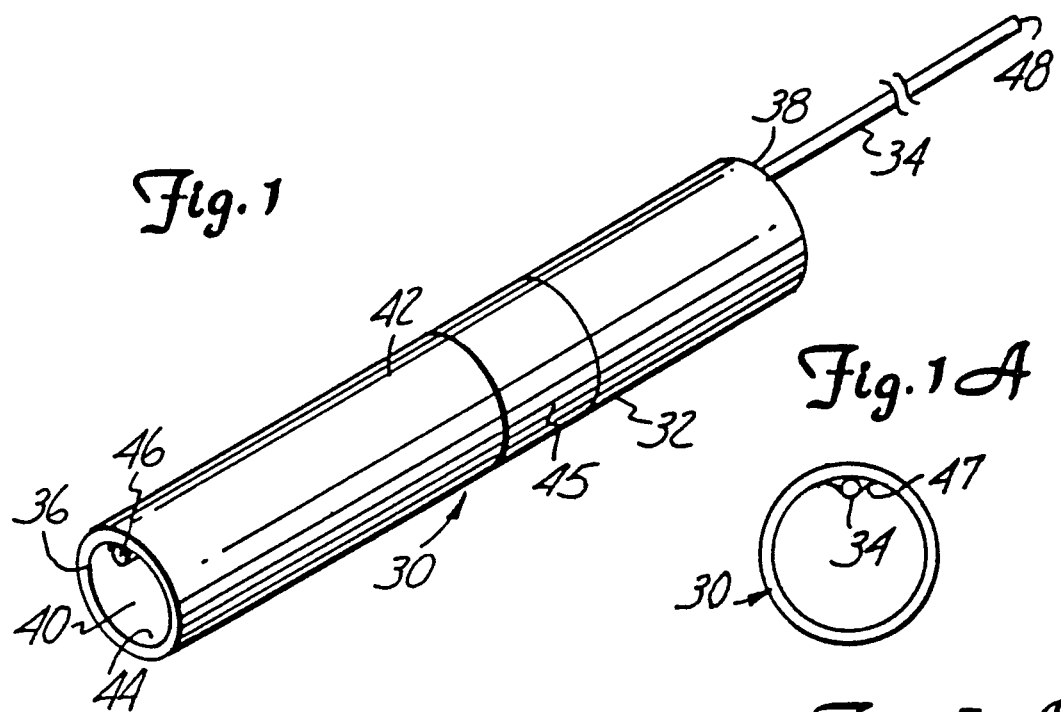
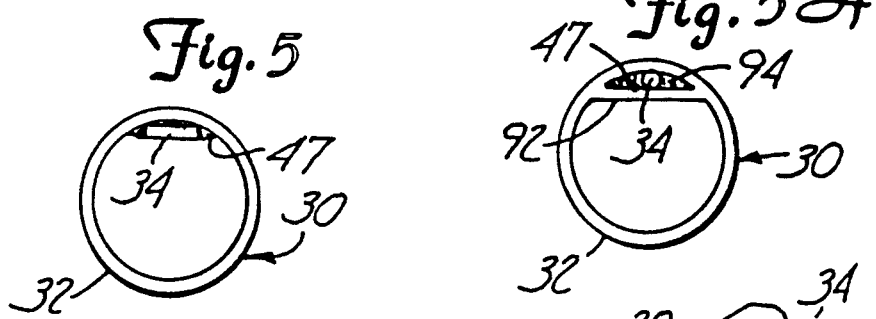
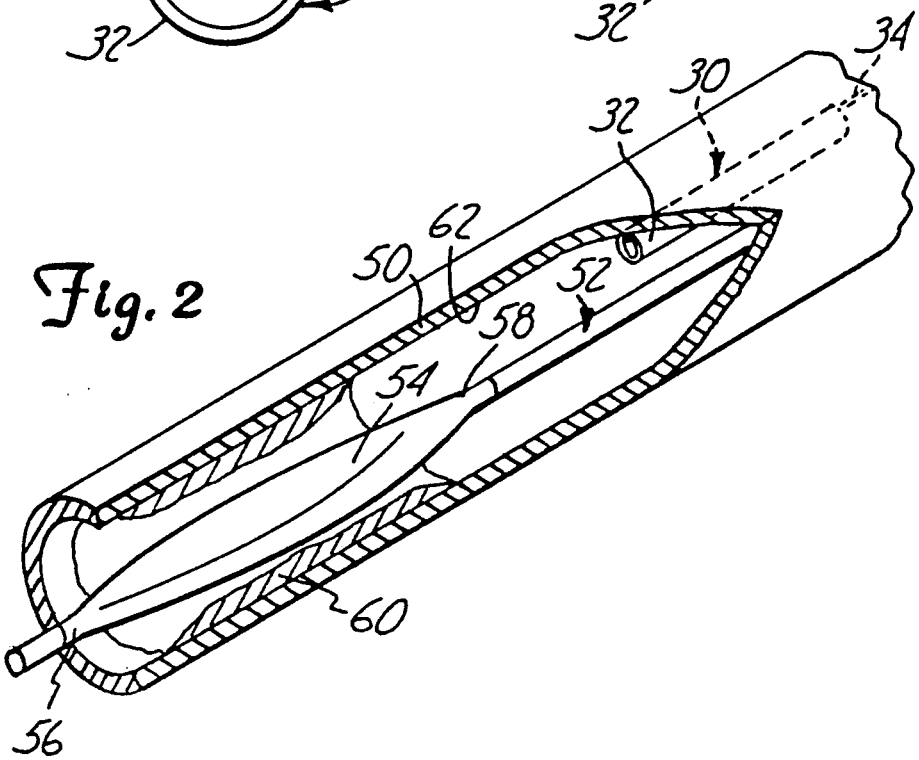

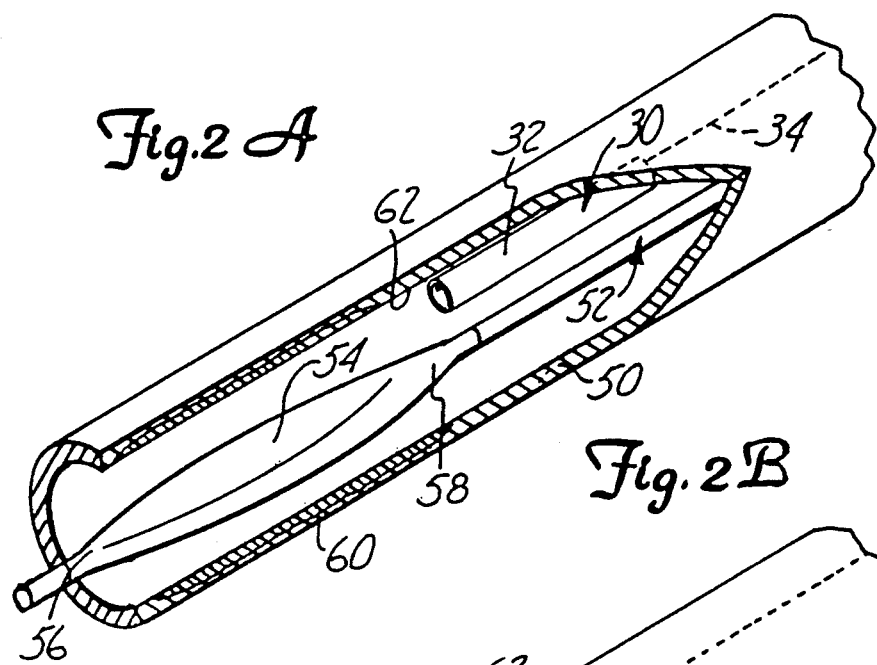
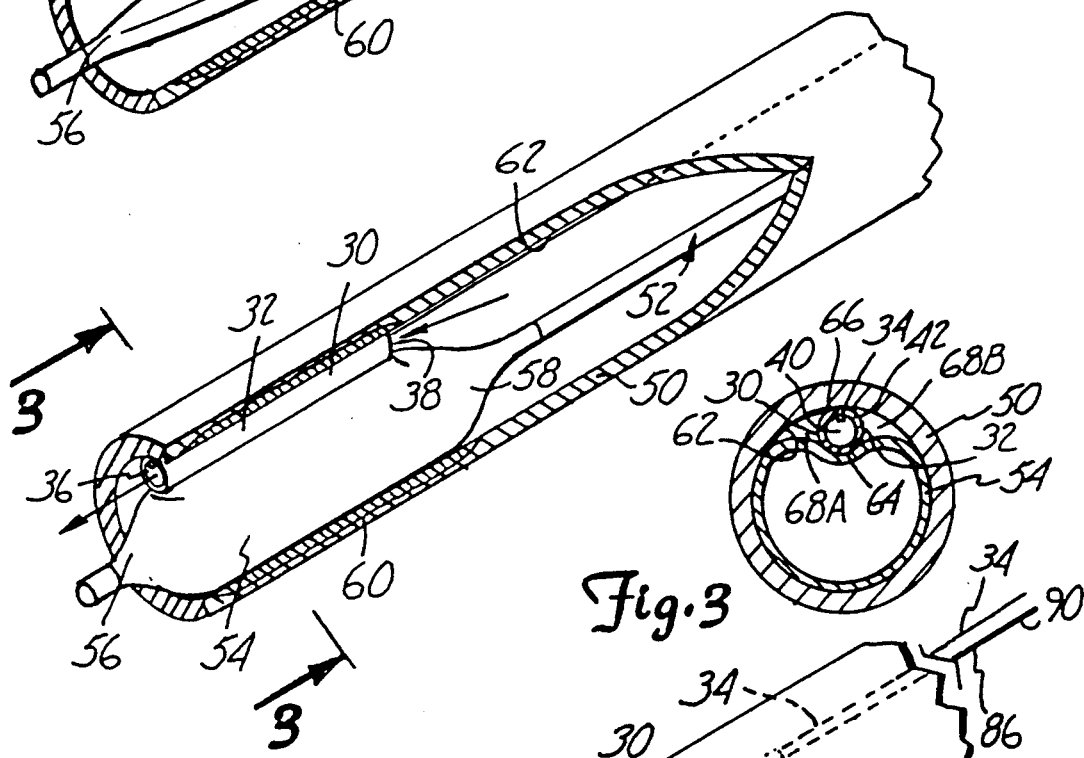
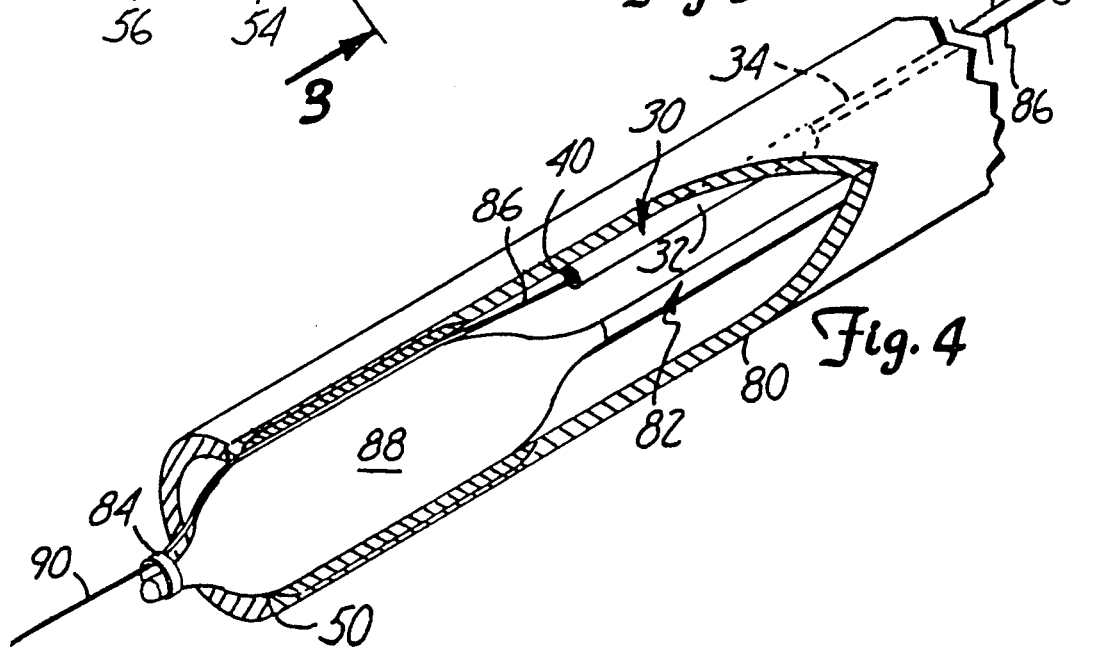

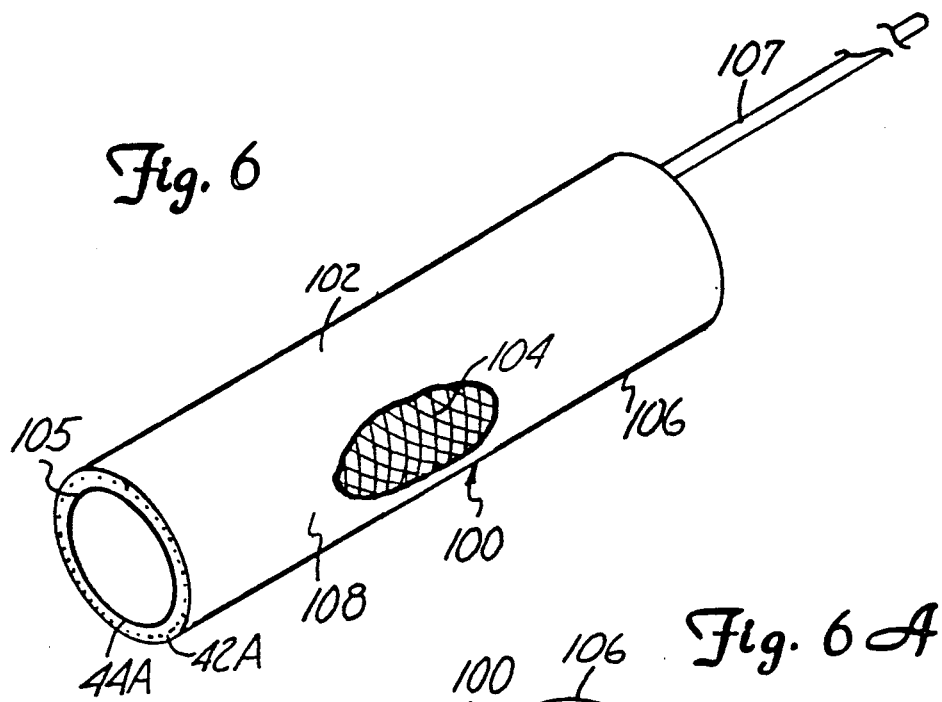
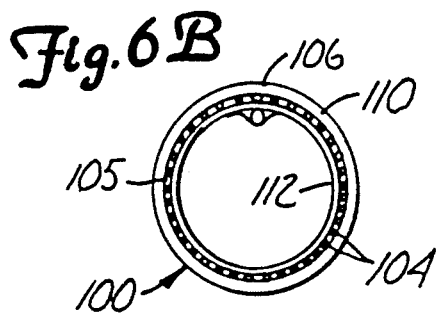
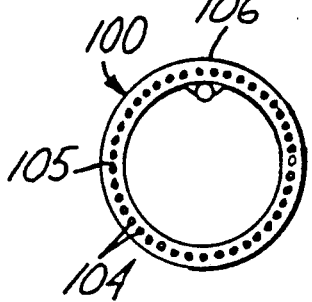
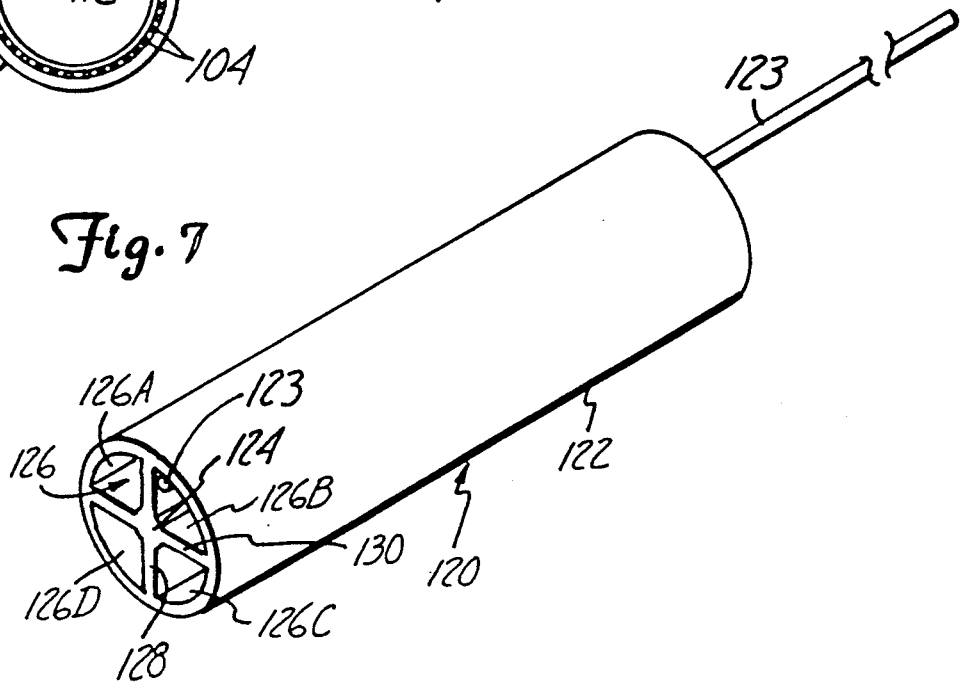

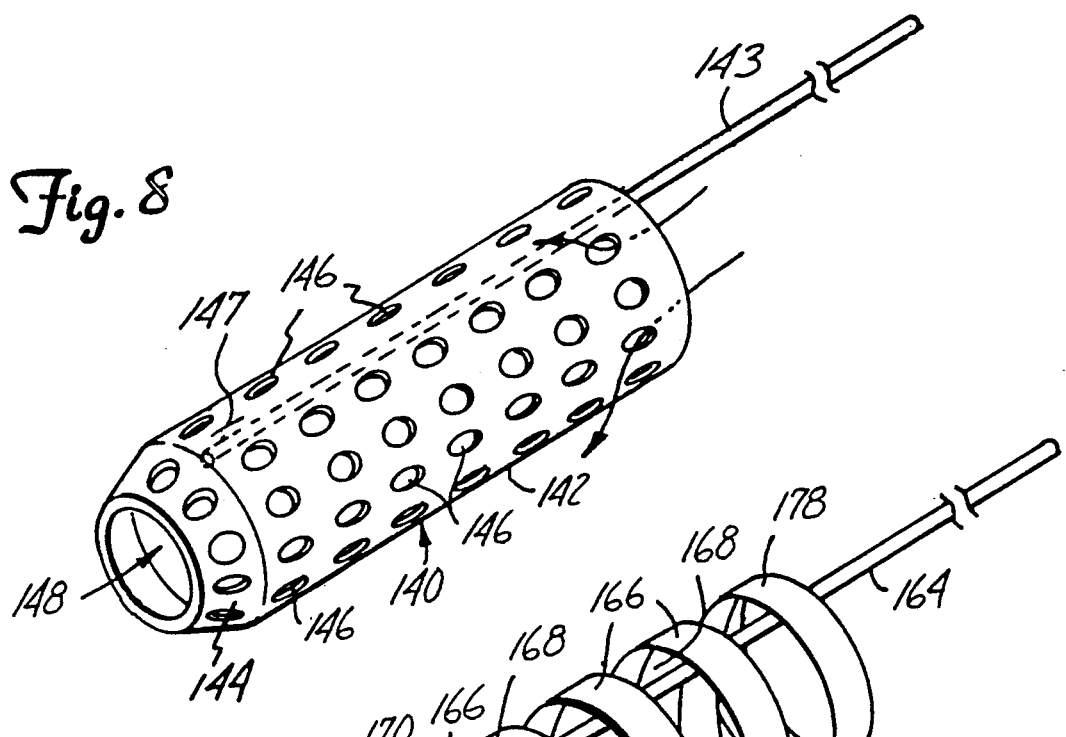
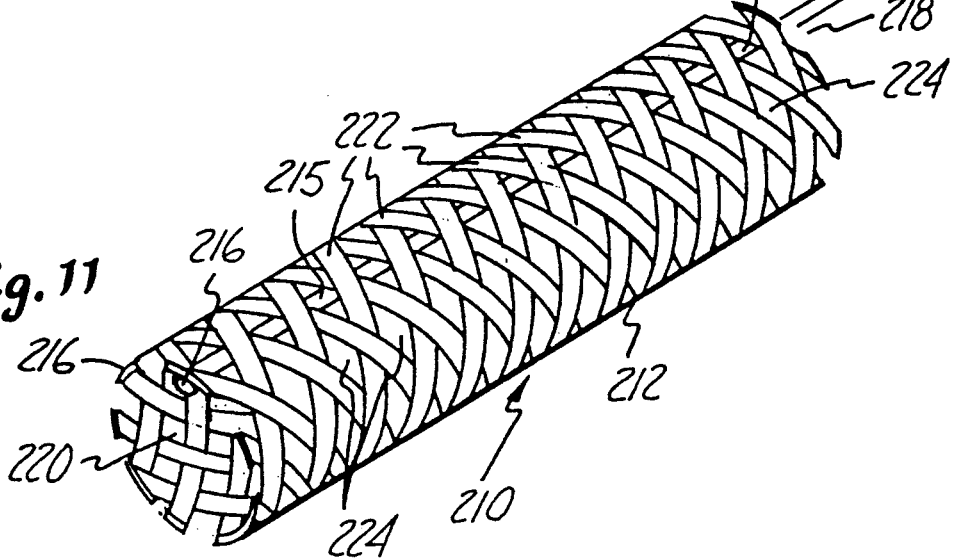

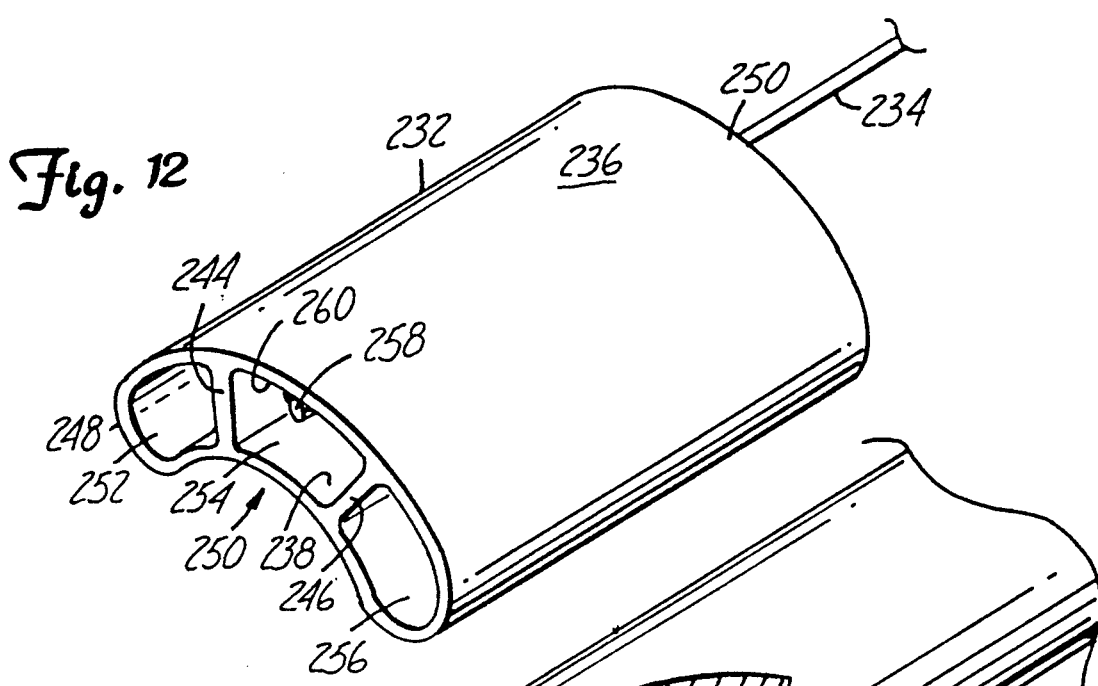
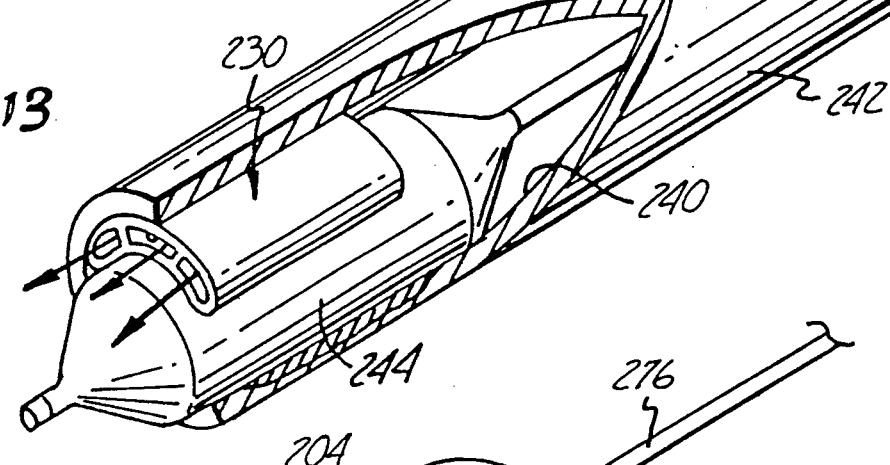
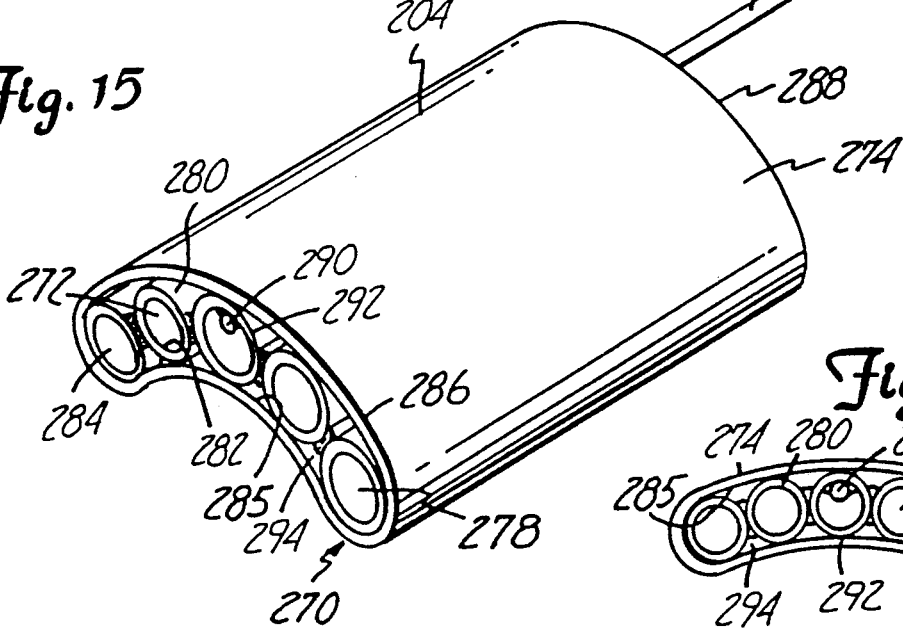

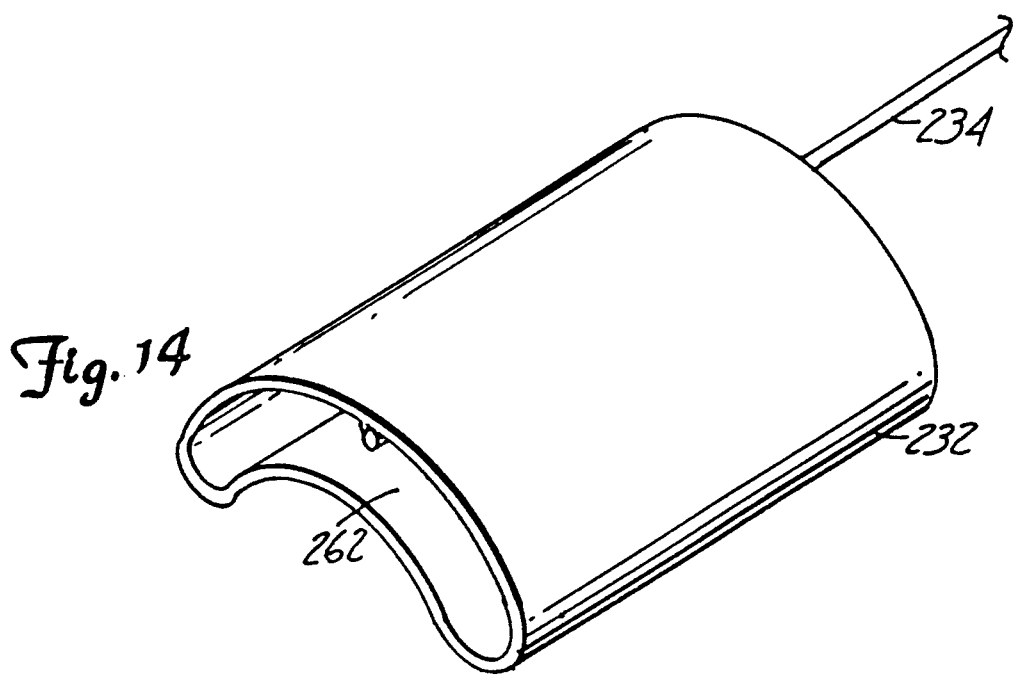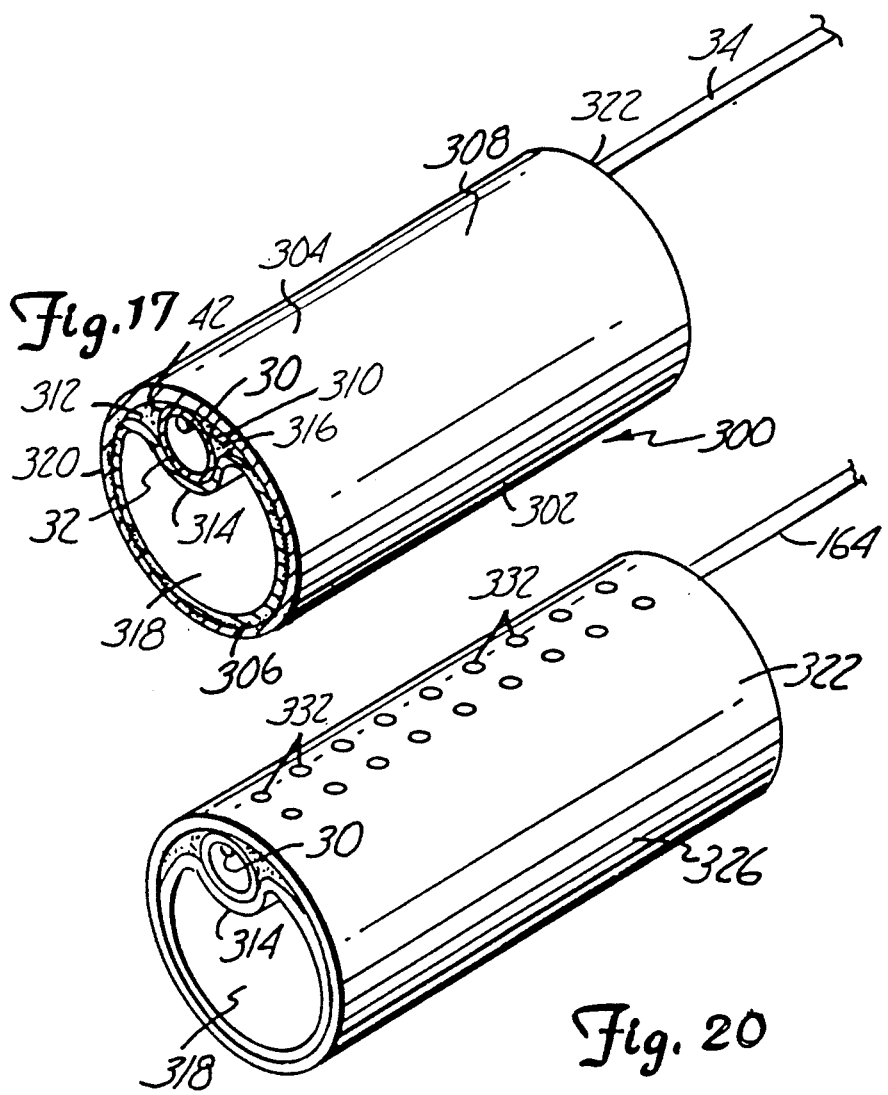

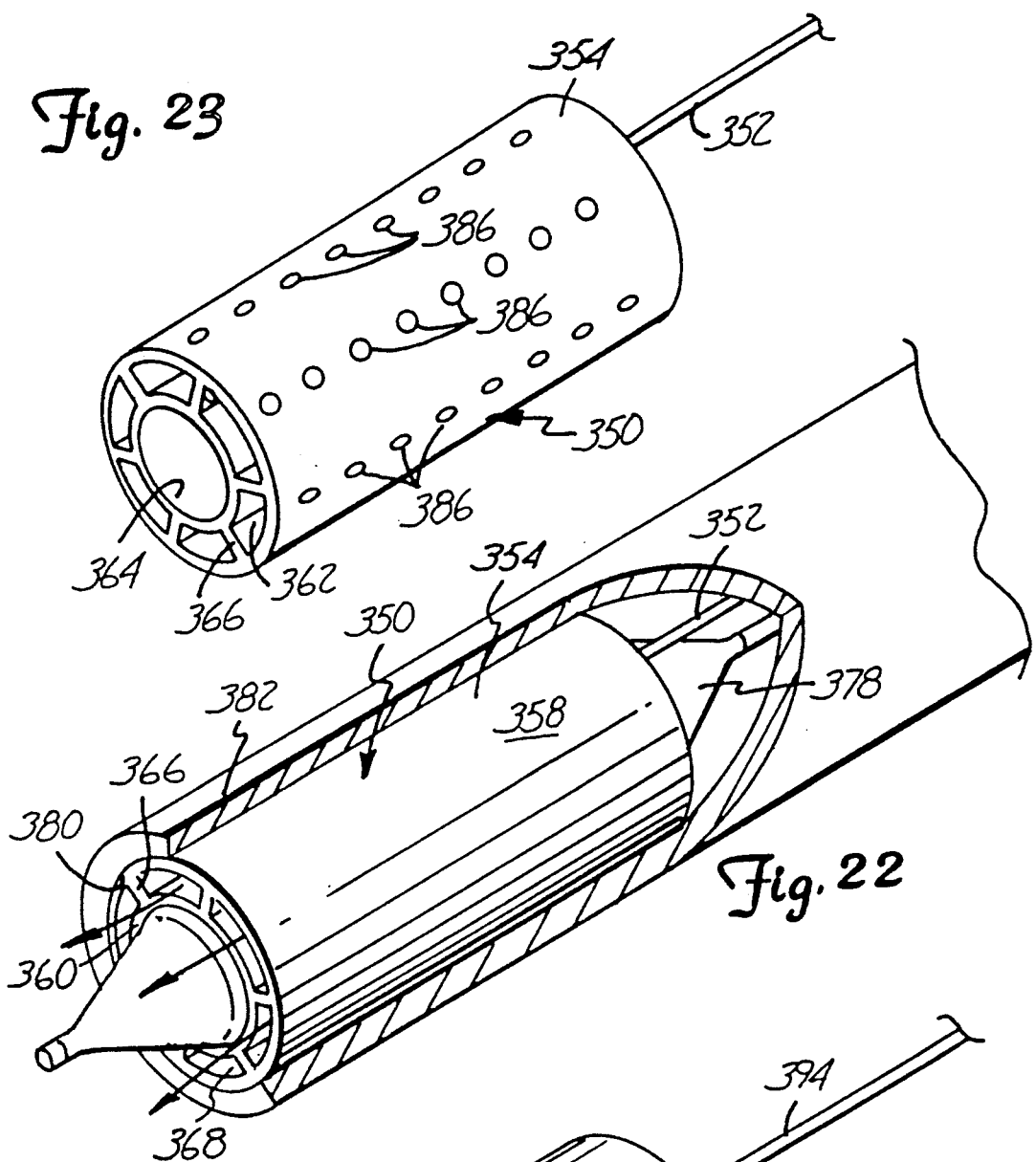
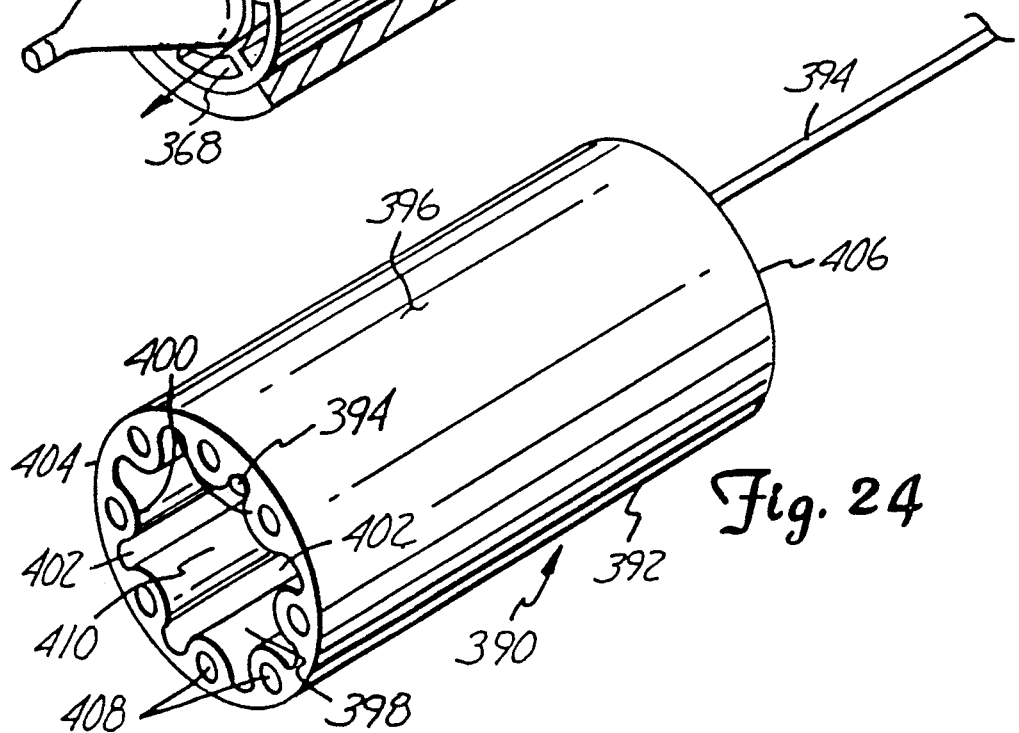

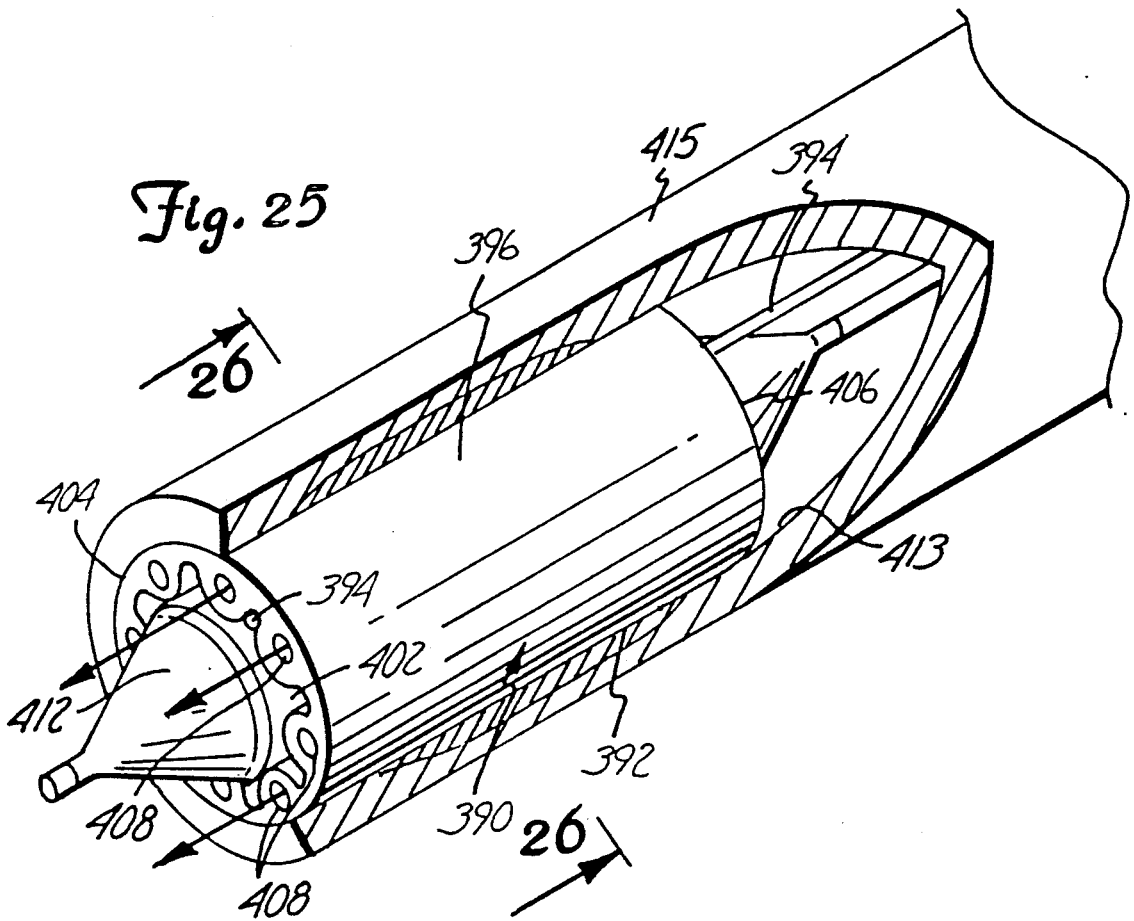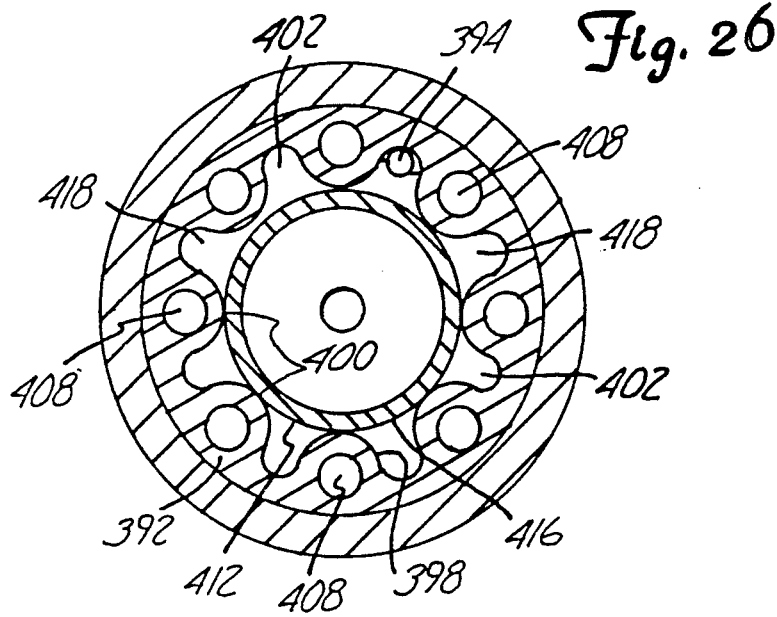

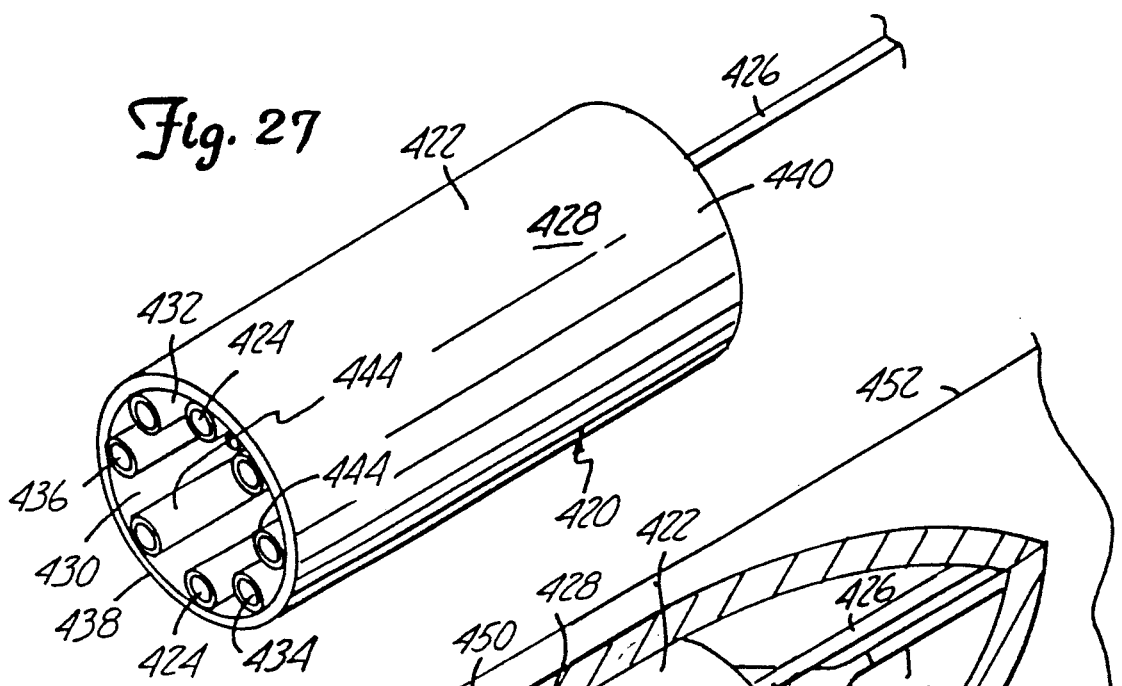
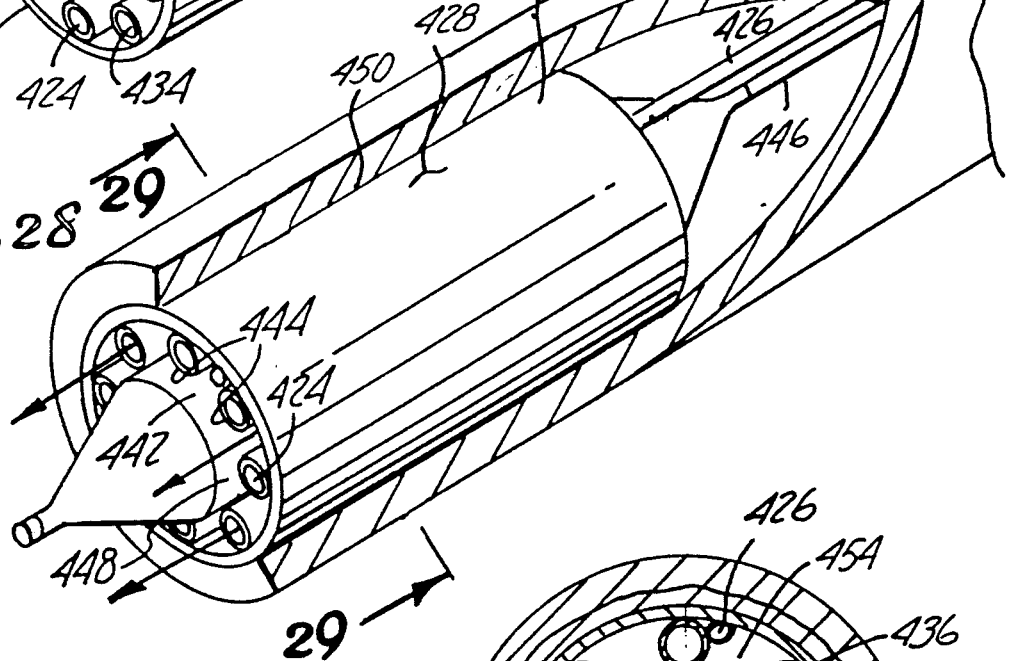
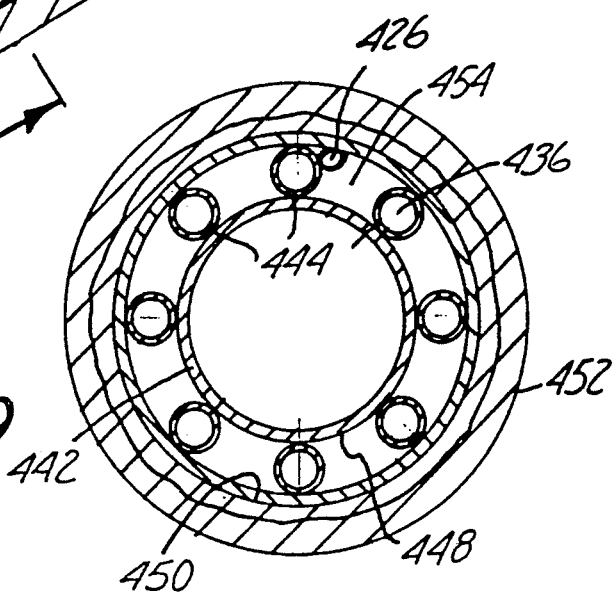

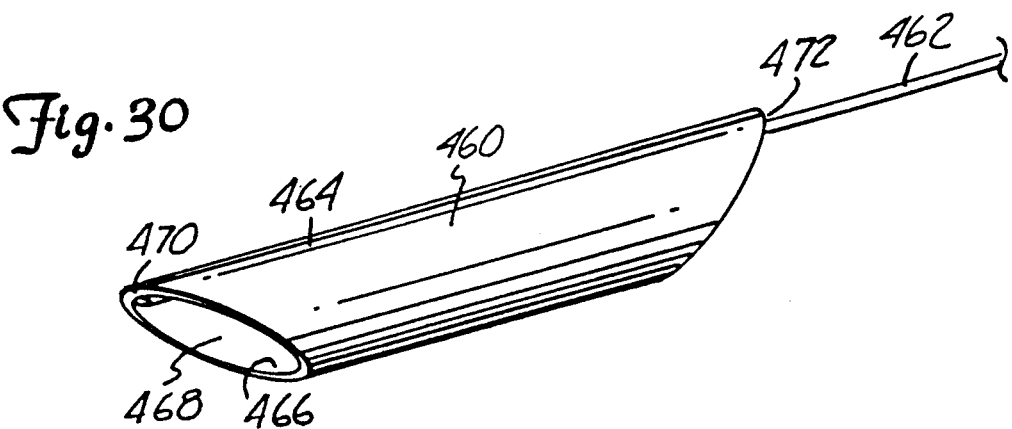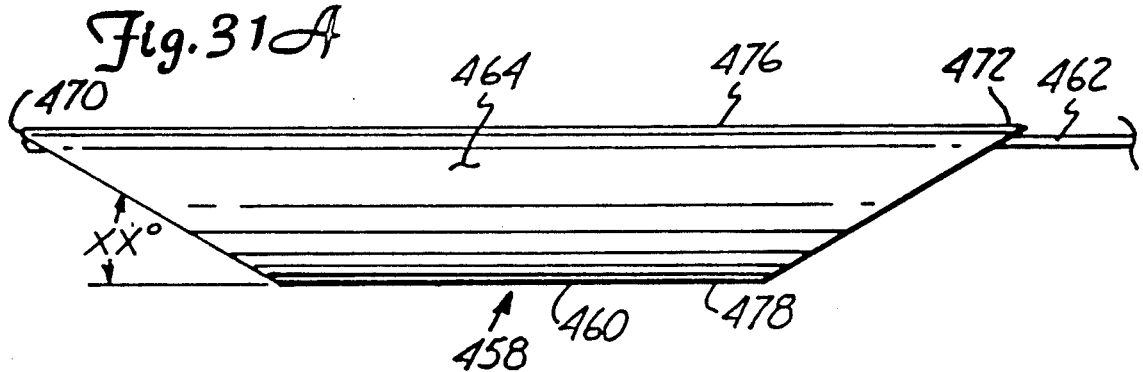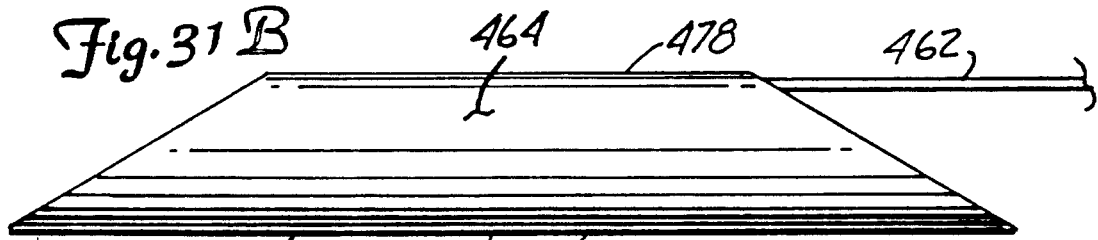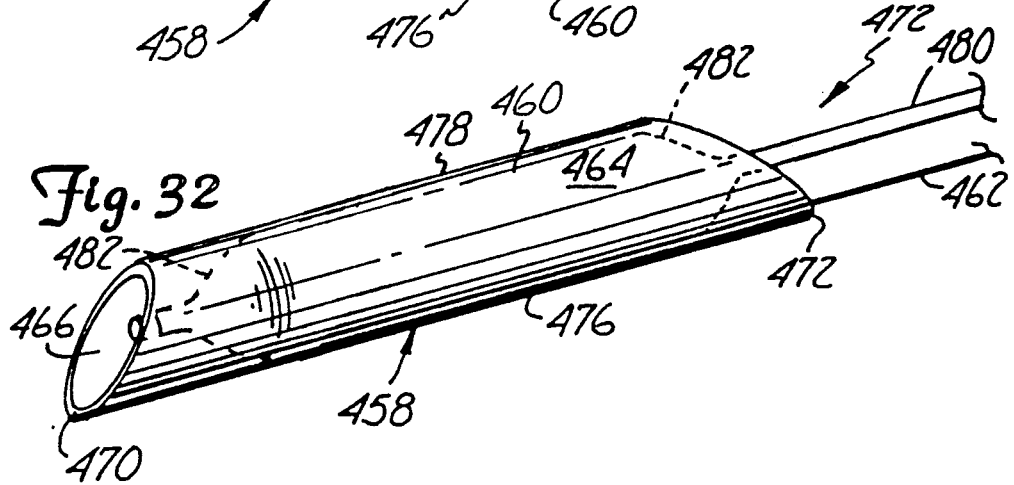

PERFORMANCE ENHANCEMENT ADAPTOR FOR INTRAVASCULAR BALLOON CATHETER

BACKGROUND OF THE INVENTION

The present invention relates to the field of intravascular balloon catheters. In particular, the present invention relates to an adaptor which is able to modify the performance of an intravascular balloon catheter to suit a variety of vascular conditions.

Intravascular balloon catheters have been effectively used to treat various maladies associated with the vascular system. For instance, angioplasty has gained wide acceptance as an efficient, effective and alternative method of removing undesirous restrictions caused by tissue growth or lesions on the inner walls of the blood vessels. Such tissue growth or lesions cause a narrowing of the blood vessels called a "stenosis," which severely restricts or limits the flow of blood.

In the most widely used form of angioplasty, a dilatation catheter, which has an inflatable balloon at its distal end, is carefully guided through the vascular system. This guiding process is arduous and time intensive. With the aid of fluoroscopy, a physician is able to position an uninflated balloon across the stenosis. The balloon, often made of a compliant material, is then inflated by applying fluid pressure through an inflation lumen of the catheter to the balloon. The radial size of a compliant balloon is a function of the inflation pressure supplied to the balloon. In other words, the greater the inflation pressure, the greater the radial size of the compliant balloon. This feature of a compliant balloon advantageously permits a physician to alter the inflation pressure (and hence the radial size of the balloon) to suit the size of the blood vessel in which the stenosis is located. Ideally, inflation of the balloon, within the balloon's working inflation pressure range, cracks and compresses the stenosis-causing lesion toward the artery wall to remove the constriction and re-establish acceptable blood flow through the artery.

Some physicians, however, prefer to use a dilatation catheter, under some circumstances, which has a balloon made of a relatively non-compliant material (i.e., a balloon which will retain a given radial size as inflation pressure is increased).

It is often desirable to keep the balloon inflated within the artery for relatively significant periods of time. One disadvantage of many dilatation catheters of the prior art is the complete occlusion of the blood vessel that results while the balloon is inflated. Prolonged complete blockage of a coronary artery results in discomfort to the patient and poses serious risk of damage to the tissue downstream from the occlusion which is deprived of oxygenated blood. These consequences limit the length of time the balloon can remain expanded within an artery to effectively re-open the artery.

Various means for providing passive perfusion of blood through or past the inflated balloon have been permanently incorporated into either the catheter shaft or the balloon. Examples of such perfusion catheters are found in the following prior art references: Baran et al. U.S. Pat. No. 4,423,725; Sahota U.S. Pat. No. 4,581,017; Hershenson U.S. Pat. No. 4,585,000; Horzewski et al. U.S. Pat. No. 4,771,777; Mueller et al U.S. Pat. 4,790,315; Songer et al. U.S. Pat. No. 4,892,519; Goldberger U.S. Pat. No. 4,909,252; Sogard et al. U.S. Pat. No. 4,944,745; Sahota U.S. Pat. No. 4,983,167; Boussignac et al. U.S. Pat. No. 5,000,734; Patel U.S. Pat. No. 5,000,743; Bonzel U.S. Pat. No. 5,002,531; and Sahota European Patent Application 0 246 998.

While perfusion catheters are capable of performing perfusion during balloon dilatation, certain drawbacks exist. For instance, the profile of perfusion catheters is generally considerably larger than that of an ordinary balloon dilatation catheter. The larger profile of perfusion catheters can inhibit and/or prohibit such a catheter from crossing a stenosis, especially when the stenosis is quite narrow. In addition, perfusion catheters known in the art are not capable of providing blood flow to side branches of the artery which occasionally are blocked by the inflated balloon. Finally, the need to use a perfusion catheter usually does not become apparent until after a relatively simple dilatation catheter has been used. Thus, in order to obtain perfusion capability with an intravascular catheter, the ordinary balloon dilatation catheter must be removed from the vascular system, and the arduous and time intensive task of rerouting a perfusion catheter within the vascular system must be undertaken. A replacement of a catheter such as this, under extreme circumstances, is not without adverse risks or consequences.

The ability to safely, successfully and efficiently perform dilatation of an occluded artery would be enhanced if only one relatively simple dilatation balloon catheter could be adapted to a variety of arterial conditions. Furthermore, the ability to perfuse past or to increase the burst pressure and strength of an ordinary, prepositioned dilatation balloon would save considerable economic cost, considerable time and potentially considerable discomfort to the patient.

SUMMARY OF THE INVENTION

The present invention is an adaptor for use with any intravascular balloon catheter, which adapts a balloon of the catheter to a variety of vascular conditions. The adaptor generally includes at least one hollow member, which has a length equal to or greater than a balloon of the catheter, and a thin, elongated positioning member, which permits the hollow member to be advanced within a blood vessel.

In one preferred embodiment, the adaptor is inserted into a guide catheter between the shaft of the balloon catheter and an inner wall of the guide catheter. By applying a longitudinal force to the elongated member, the adaptor is then self-guided between the catheter shaft and a wall of the artery to the balloon. With the balloon deflated, the adaptor is positioned with a surface of the adaptor adjacent a surface of the balloon such that proximal and distal ends of the hollow member are generally aligned with or equidistant to proximal and distal ends, respectfully, of the balloon. Inflation of the balloon secures the surface of the hollow member to the surface of the balloon. So positioned the hollow member supplies a performance not capable by the balloon alone.

In another embodiment, the hollow member is guided to the balloon along a guide wire which is external to the catheter shaft.

In another embodiment, the hollow member is guided to the balloon over the catheter shaft. When a manifold of the catheter is removable, the hollow member is positioned over a proximal end of the catheter shaft by removing the manifold after the catheter has been prepositioned within the artery. When the manifold is not removable, the hollow member is positioned over a distal end of the catheter shaft before the catheter is inserted into the guide catheter. The hollow member is then maintained near the manifold during the positioning of the catheter.

In one preferred embodiment, the hollow member creates a blood perfusion passage, which permits the balloon of a basic dilatation catheter to remain inflated within the artery for an extended period of time while allowing blood to flow past the balloon to tissues downstream from the balloon. Unlike perfusion dilatation catheters, which have relatively large profiles, the use of the adaptor of the present invention for perfusion enables a physician to use a relatively low profile balloon dilatation catheter to cross a blocked region of the artery.

In another embodiment, a side wall of the hollow member includes openings, which expose the blood perfusion passage and permit a flow of blood transverse to the blood perfusion passage. In the event the inflated balloon and hollow member are positioned across a side branch of the artery, the adaptor enables blood to flow into the side branch.

In another embodiment, the adaptor has sufficient longitudinal flexibility and radial rigidity to conform to a bend of the artery while maintaining the blood perfusion passage past the inflated balloon.

In another embodiment, the hollow member is made of a noncompliant material that envelopes the balloon. Upon inflation of the balloon, the hollow member serves to restrict the balloon's radial size, enhance its strength and increase the dilatation force applied to the stenosis. In addition the hollow member is capable protecting the artery in the event of a balloon rupture. Finally, the hollow member is able to decrease the size of the balloon in the event the balloon is too large for the artery requiring treatment.

When a vascular condition is encountered during a balloon catheter procedure for which the balloon catheter is ill-suited, the adaptor of the present invention provides a simple and inexpensive means to achieve a desired performance that would not have been possible by the balloon alone. Use of the hollow member therefore avoids the need for the arduous and time intensive complete exchange of the balloon catheter to accomplish the desired performance.

BRIEF DESCRIPTION OF THE DRAWINGS

FIG. 1 is a perspective view of a first embodiment of the adaptor of the present invention.

FIG. 1A is an end view of the adaptor shown in FIG. 1.

FIGS. 2-2B are perspective views of an artery with a section cut away to demonstrate use of the adaptor of FIG. 1 with a balloon catheter.

FIG. 3 is a cross-sectional view of the adaptor of FIG. 2B taken along line 3—3.

FIG. 4 is a perspective view of an artery with a section cut away showing an alternate method of guiding the adaptor of FIG. 1 through an artery.

FIG. 5-5A are end views of the adaptor shown in FIG. 1 showing alternate connections between the hollow member and the positioning member.

FIG. 6 is a perspective view of a second embodiment of the adaptor of the present invention with a section cut away to show reinforcing fibers embedded in the wall of the adaptor.

FIG. 6A is a cross-sectional view of the adaptor of FIG. 6 taken along line 6A—6A.

FIG. 6B is a cross-sectional view of an alternative embodiment of the adaptor of FIG. 6.

FIG. 7 is a perspective view of a third embodiment of the adaptor of the present invention.

FIG. 8 is a perspective view of a fourth embodiment of the adaptor of the present invention.

FIG. 9 is a perspective view of a fifth embodiment of the adaptor of the present invention.

FIG. 11 is a perspective view of a sixth embodiment of the adaptor of the present invention.

FIG. 12 is a perspective view of a seventh embodiment of the adaptor of the present invention.

FIG. 13 is a perspective view of an artery with a section cut away showing the adaptor of FIG. 12 secured between an inflated balloon and a wall of the artery.

FIG. 14 is a perspective view of the adaptor of FIG. 12 with the support ribs removed.

FIG. 15 is a perspective view of an eighth embodiment of the adaptor of the present invention.

FIG. 16 is a cross-sectional view of the adaptor of FIG. 15 taken along line 15—15.

FIG. 17 is a perspective view of a ninth embodiment of the adaptor of the present invention, which incorporates a sleeve.

FIG. 20 is a perspective view of the sleeved adaptor of FIG. 17 with openings through the sleeve.

FIG. 22 is a perspective view of an artery with a section cut away showing the adaptor of FIG. 21 secured between a balloon and a wall of the artery.

FIG. 23 is a perspective view of the adaptor of FIG. 21 with openings through an exterior of the adaptor.

FIG. 24 is a perspective view of an eleventh embodiment of the adaptor of the present invention.

FIG. 25 is a perspective view of an artery with a section cut away showing the adaptor of FIG. 24 secured between a balloon and a wall of the artery.

FIG. 26 is a cross-sectional view of the adaptor of FIG. 24 taken along line 26—26.

FIG. 27 is a perspective view of a twelfth embodiment of the adaptor of the present invention.

FIG. 28 is a perspective view of an artery with a section cut away showing the adaptor of FIG. 27 secured between a balloon and a wall of the artery.

FIG. 29 is a cross-sectional view of the adaptor of FIG. 27 taken along line 29—29.

FIG. 30 is a perspective view of a thirteenth embodiment of the adaptor of the present invention.

FIGS. 31A-31B are side views of the adaptor of FIG. 30.

FIG. 32 is a perspective view of the adaptor of FIG. 30 shown positioned over an inflated balloon.

DETAILED DESCRIPTION OF THE PREFERRED EMBODIMENTS

Perfusion Adaptor 30 (FIGS. 1-5A)

Figure 4A:
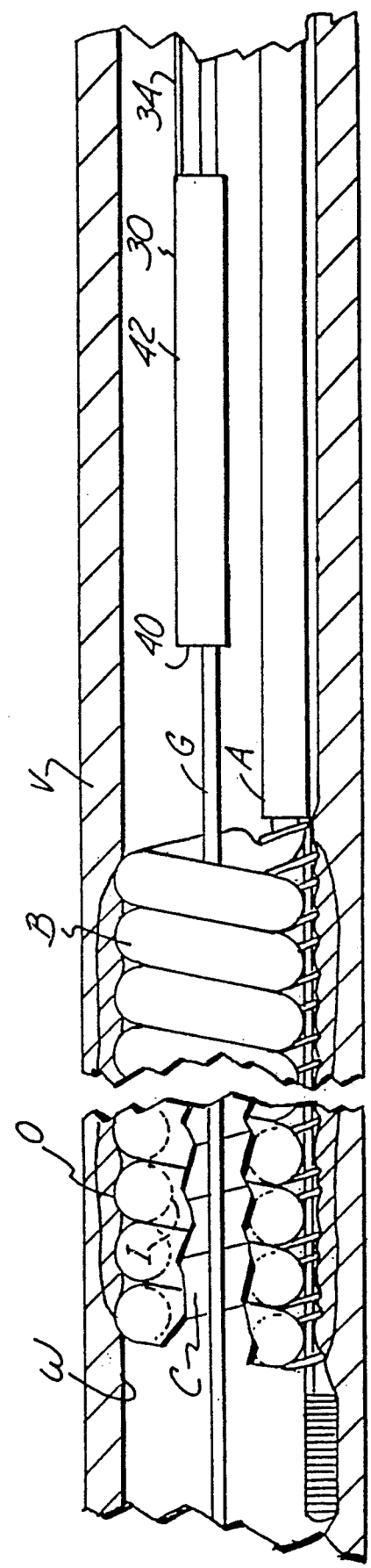
FIG. 4A is an enlarged side view of a distal region of a balloon catheter, with a portion of balloon B cut away, to demonstrate another alternative method of using the adaptor of FIG. 1 with a donut-shaped balloon.

FIG. 1 is a perspective view of perfusion adaptor 30 of the present invention. Perfusion adaptor 30 generally includes hollow member 32 and positioning member 34. Hollow member 32 particularly includes distal end 36, proximal end 38, outer surface 42, inner surface 44 and flow passage 40, which extends from distal end 36 to proximal end 38. As shown in FIG. 1, perfusion adaptor 30 is generally tubular-shaped, with outer surface 42 and inner surface 44 being generally cylindrical. Hollow member 32 also includes radiopaque marker 45, as is known in the art, to provide the physician with a visual reference for accurately positioning hollow member 32 within an artery.

Hollow member 32 has a length equal to or greater than balloons typically used in balloon catheter procedures (i.e., balloons about 10 millimeters to about 50 millimeters long). In one preferred embodiment, hollow member 32 also has an outer diameter which ranges from about 0.010 to about 0.150 inches, and a wall thickness which ranges from about 0.001 inch to about 0.006 inch. The relatively small size of hollow member 32, therefore, makes hollow member 32 well suited to be positioned between a wall of an artery and an inflated balloon without dramatically altering the geometry of the artery. On the other hand, the size of flow passage 40 is adequately large to permit a sufficient amount of blood to flow past an inflated balloon to supply tissues downstream from the balloon, and to minimize the potential for discomfort of the patient in the event the balloon must remain inflated within the artery for an extended period of time.

Hollow member 32 is preferably made of a material or materials, which impart axial flexibility and radial rigidity to hollow member 32. Hollow member 32 is axially flexible to permit hollow member 32 to be advanced through relatively tortuous paths often encountered during intravascular catheter procedures. Hollow member 32 is also radially rigid to prevent flow passage 40 from collapsing when hollow member 32 is positioned between artery wall 62 and inflated balloon 54 (as shown in FIG. 2D and 3). In one embodiment, hollow member 32 of the present invention is extruded from a suitable polymer, such as polyethylene.

Positioning member 34 is an elongated structure which includes distal end 46 and proximal end 48. As shown in FIGS. 1-1A, distal end 46 is generally aligned with distal end 36 of hollow member 32, and positioning member 34 is bonded to inner surface 44 with bonding material 47, such as the epoxy UR3507 from H. B. Fuller. In preferred embodiments, positioning member 34 is made of 304 stainless steel or any shape memory metal alloy, such as NITINOL (nickel titanium alloy). Positioning member 34 has a length greater than typical balloon catheters (i.e., greater than about 130 centimeters), and suitable pushable characteristics to allow hollow member 32 to be advanced within a blood vessel, between a balloon catheter and a wall of the blood vessel, to the balloon of the balloon catheter. In preferred embodiments, positioning member 34 has an outer diameter of about 0.006 to about 0.018 inches.

First Method of Use

FIGS. 2-2B best show one preferred method of using perfusion adaptor 30 of the present invention. FIGS. 2-2B show a perspective view of artery 50 with a section cut away to show standard balloon dilatation catheter 52 positioned within artery 50. For purposes of describing the use of perfusion adaptor 30, balloon 54, which includes distal end 56 and proximal end 58, is positioned adjacent lesion 60 of artery wall 62, as shown in FIG. 2. Perfusion adaptor 30 is inserted into a guide catheter (not shown), which is used in conjunction with catheter 52. Hollow member 32 is then advanced through artery 50 by applying a pushing force to positioning member 34. In one embodiment, perfusion adaptor 30 is self-guiding, with radiopaque marker 45 providing visual feedback necessary to determine the location of hollow member 32 within artery 50.

As is commonly known, inflation of balloon 54 compresses lesion 60, thereby re-opening artery 50, as shown in FIG. 2A. In some instances, adequate compression of lesion 60 is achieved by inflating balloon 54 for a relatively short period of time. In other instances, however, it is desirable or necessary to permit balloon 54 to remain inflated within artery 50 for a period of time which is significant enough to cause extended depletion of oxygen bearing blood downstream from inflated balloon 54. In such instances, where prolonged inflation of balloon 54 within artery 50 is desired or required, balloon 54 is deflated, as shown in FIG. 2A. With balloon 54 deflated, a physician advances hollow member 32 adjacent balloon 54 by applying an appropriate longitudinal force to positioning member 34.

As shown in FIG. 2B, hollow member 32 is positioned with distal end 36 of hollow member 32 generally aligned with distal end 56 of balloon 54, and with proximal end 38 of hollow member 32 generally aligned with proximal end 58 of balloon 54. Balloon 54 is reinflated, thereby re-exerting a dilatation force to artery wall 62 and further securing hollow member 32 between balloon 54 and artery wall 62. With hollow member 32 positioned between balloon 54 and artery wall 62, flow passage 40 permits a flow of blood past balloon 54, thereby permitting balloon 54 to remain inflated with artery 50 for an extended period of time.

FIG. 3 is a cross-sectional view of balloon 54 and perfusion adaptor 30 taken along line 3—3 of FIG. 2B. As shown in FIG. 3, balloon 54 contacts outer surface 42 of hollow member 32 at first side 64, thereby securing outer surface 42 of hollow member 32 against artery wall 62 at second side 66. An outer surface of balloon 54 contacts a substantial portion of artery wall 62 which, due to inflation pressures within the balloon, dilates artery 50. As further shown in FIG. 3, with hollow member 32 inflated between balloon 54 and artery wall 62, sinuses 68A and 68B are formed adjacent hollow member 32. Sinuses 68A and 68B are formed by the interaction of balloon 54, artery wall 62 and outer surface 42 of hollow member 32 from distal end 36 to proximal end 38 of hollow member 32. Sinuses 68A and 68B permit additional flow of blood past balloon 54 when balloon 54 is inflated within artery 50. As further shown in FIG. 3, positioning member 34 occupies a relatively small cross-sectional area of flow passage 40 so as not to interfere with the flow of blood through flow passage 40.

Second Method of Use

FIG. 4 shows an alternate method for advancing perfusion adaptor 30 through an artery. Generally, balloon catheters are known in the art which have a guide wire guide positioned external to and at a distal end of the catheter shaft. The distal guide wire guide allows a guide wire over which the catheter is guided to remain external to the catheter shaft along the entire length of the shaft. This enables a physician to exchange one catheter for another without interrupting the established position of the guide wire across a stenosis of the artery. Examples of such catheters include the following, which are incorporated by reference: Giesy et al. U.S. Pat. No. 4,824,435, European Patent Application 0 344 530 A1 by Advanced Cardiovascular Systems, Inc., and co-pending U.S. Pat. applications Ser. No. 07/782,518 entitled COILED, PERFUSION BALLOON CATHETER, filed Oct. 25, 1991 by M. Arney, and Ser. No. 07/866,998 entitled BALLOON CATHETER FOR DILATATION AND PERFUSION, filed Apr. 9, 1992 by M. Arney.

Perfusion adaptor 30 can alternatively be guided through a vessel over a guide wire of the aforementioned catheter design. FIG. 4 is a perspective view of artery 80 with a section cut away to show balloon catheter 82, which includes distal guide wire guide 84 and guide wire 86. As shown in FIG. 4, perfusion adaptor 30 can be easily advanced over guide wire 86 to balloon 88 by sliding flow passage 40 of hollow member 32 over proximal end 90 of guide wire 86 and then applying a pushing force to positioning member 34. The location of guide wire guide 84 at the distal end of catheter 82 ensures that perfusion adaptor 30 can be advanced only as far as balloon 88. The nominal size of guide wire 86 ensures that flow passage 40 retains adequate flow space for the flow of blood through hollow member 32.

Third Method of Use

FIG. 4A gives an enlarged side view of a distal region of balloon catheter A, with a portion of balloon B cut away to demonstrate another alternative method of using adaptor 30 with a donut-shaped balloon. Donut-shaped balloons are described in detail in the following previously disclosed references: Goldberger U.S. Pat. No. 4,909,252; Bonzel U.S. Pat. No. 5,002,531; and co-pending U.S. Pat. application Ser. No. 07/782,518. The detailed descriptions of the aforementioned references are incorporated by reference herein.

As shown in FIG. 4A, balloon B includes outer surface O, inner surface I and cylindrical space C, which is defined by inner surface I. Cylindrical space C provides a space to accommodate guidewire G and allows balloon B of catheter A to be guided over guidewire G within an artery. With guidewire G positioned within cylindrical space C, adaptor 30 is guidable over guidewire G in a manner similar to that described relative to FIG. 4.

As further shown in FIG. 4A, as balloon B is inflated within blood vessel V, outer surface O radially expands outward and engages wall W of blood vessel V. In addition, inflation of balloon B causes inner surface I to radially expand inward toward guidewire G. In order to halt the inward radial expansion of inner surface I and therefore increase the outward radial dilatation force of outer surface O, adaptor 30 is advanced along guidewire G and positioned within cylindrical space C, with distal end 36 and proximal end 38 of adaptor 30 generally aligned or extending equal distances from proximal and distal ends of balloon B, respectfully. With balloon B partially inflated, cylindrical space C has a diameter which is slightly larger than an outer diameter of hollow member 32, which allows adaptor 30 to be easily maneuvered within cylindrical space C along guidewire G. Further inflation of balloon B causes inner surface I to engage outer surface 42 of adaptor 30, which allows the dilatation force of balloon B to be directed to outer surface O and against wall W of blood vessel V. Furthermore, flow passage 40 of adaptor 30 permits blood to flow past balloon B for as long as balloon B remains inflated within blood vessel V.

As shown in FIG. 5, connection of positioning member 34 to hollow member 32 may be enhanced by flattening a distal portion of positioning member 34 to provide greater surface contact over which bonding material 47 can adhere. As shown in FIG. 5A, hollow member 32 may alternatively include rib 92 so as to create bonding chamber 94 for positioning member 34. Bonding chamber 94 provides a 360° bonding surface for bonding material 47, which ensures a secure connection between positioning member 34 and hollow member 32.

Perfusion Adaptor 100 (FIG. 6-6B)

FIG. 6 is a perspective view of perfusion adaptor 100, which includes all of the features of perfusion adaptor 30 plus support structure 102. A section of FIG. 6 is cut away to better show support structure 102. Support structure 102 is comprised of reinforcing fibers 104, which are woven in the shape of a tube. In the preferred embodiment, as shown in FIG. 6-6A, support structure 102 is embedded into wall 105 by introducing support structure 102 during the extrusion of hollow member 106. Positioning member 107 is attached to hollow member 106 as described previously.

Reinforcing fibers 104 are preferably made of stainless steel or nylon. Alternatively, reinforcing fibers 104 can be a radiopaque metal, such as titanium or a platinum alloy, which allows the physician to monitor the positioning of perfusion adaptor 100 within an artery. Support structure 102 enhances the axial flexibility and radial rigidity of hollow member 106, thereby enhancing the maneuverability of perfusion adaptor 100 while ensuring the flow passage remains open under the force of the balloon.

Support structure 102 can also be associated with hollow member 106 in a variety of alternative ways. For example, as shown in FIG. 6B, support structure 102 is incorporated into hollow member 106 by bonding support structure 102 between outer layer 110 and inner layer 112 of hollow member 106. Alternatively, support structure 102 can be positioned over outer surface 108 of hollow member 106 and secured by any suitable bonding material.

Perfusion Adaptor 120 (FIG. 7)

FIG. 7 is a perspective view of perfusion adaptor 120 of the present invention. Perfusion adaptor 120, which consists of hollow member 122 and positioning member 123, includes all the features of perfusion adaptor 30, but hollow member 122 additionally includes geometric support structure 124 within flow passage 126.

Geometric support structure 124 includes vertical rib 128 and horizontal rib 130. Vertical rib 128 and horizontal rib 130 are integrally formed with of hollow member 122. Geometric support structure 124 divides flow passage 126 into passages 126A, 126B, 126C and 126D. Passages 126A-126D, like flow passage 40 shown in FIG. 1, are capable of permitting a flow of blood past an inflated balloon when perfusion adaptor 120 is positioned between an artery wall and an inflated balloon as shown in FIG. 2B and 3.

In the preferred embodiment, geometric support structure 124 is made of the same material as and coextruded with hollow member 122. Alternatively, however, geometric support structure 124 is made of a material different than hollow member 122. In such an embodiment, hollow member 122 is made of a soft material, such as silicone, and geometric support structure 124 is made of any suitable polymer material which is capable of providing radial support and rigidity to hollow member 122.

Perfusion Adaptor 140 (FIG. 8)

FIG. 8 is a perspective view of perfusion adaptor 140 of the present invention. Perfusion adaptor 140, which includes hollow member 142 and positioning member 143, is similar to perfusion adaptor 30 shown in FIG. 1; however, perfusion adaptor 140 includes two additional features. First, hollow member 142 includes tapered distal region 144, which presents a less traumatic distal end to hollow member 142 and enhances the safe advancement of perfusion adaptor 140 through the vascular system.

Second, hollow member 142 includes a multiplicity of holes 146, which are spaced about and extend through outer surface 147 of hollow member 142. Holes 146 are formed by punching or drilling holes in a generally equally spaced manner about outer surface 147. Each hole 146 ranges in diameter from about 0.005 inch to about 0.050 inch. Holes 146 permit blood flowing through flow passage 148 to flow in a direction generally transverse to flow passage 148 when perfusion adaptor 140 is positioned across a side branch of an artery as shown in FIG. 10A. This enables blood to flow into the artery side branch. Heparinization of the patient, as is known in the art, ensures that holes 146 remain open for as long as a balloon remains inflated across the side branch.

Figure 10:
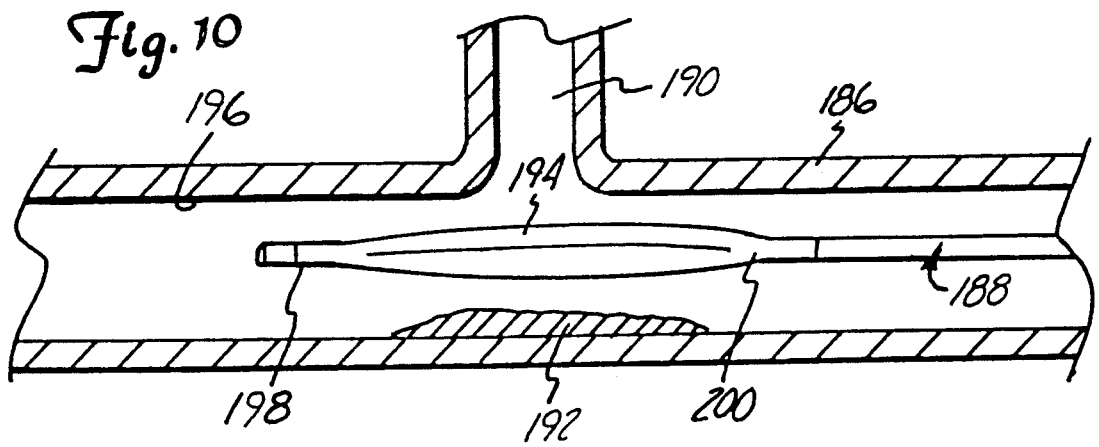
FIG. 10 is a sectional view of a side branch intersection of an artery with a balloon catheter, shown in perspective, positioned across the side branch.
Figure 10A:
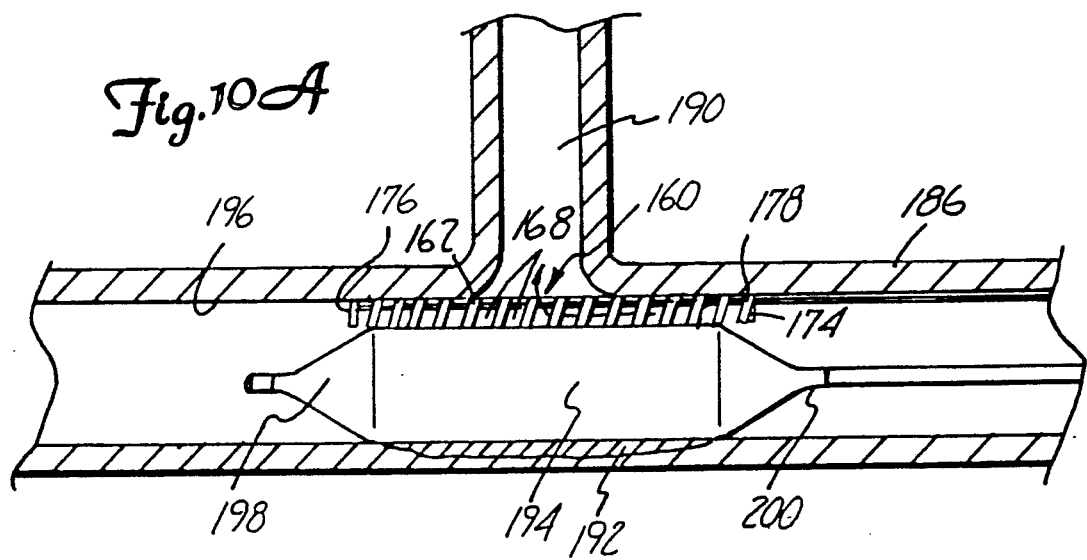
FIG. 10A is a sectional view of the artery shown in FIG. 10, with the adaptor of FIG. 9 secured across the side branch by an inflated balloon.
Figure 10B:
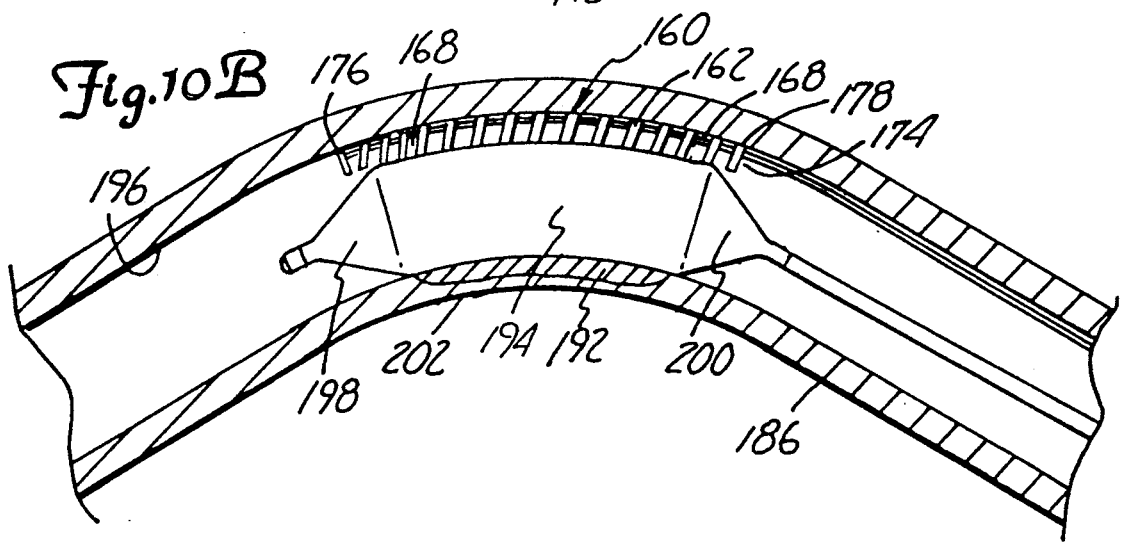
FIG. 10B is a sectional view of a bend of an artery showing the adaptor of FIG. 7 secured between an inflated balloon and a wall of the artery.

Perfusion Adaptor 160 (FIGS. 9-10B)

FIG. 9 is a perspective view of perfusion adaptor 160 of the present invention. Perfusion adaptor 160 generally includes coil member 162 and positioning member 164.

Coil member 162 is comprised of a series of individual coils 166, with each coil 166 separated from an adjacent coil by space 168. Each coil 166 has outer surface 170 and inner surface 172. Collectively, inner surfaces 172 define a generally cylindrical flow passage 174, which extends from distal end 176 to proximal end 178 of coil member 162.

Positioning member 164 is similar to positioning member 34 shown in FIG. 1 except that positioning member 164 includes spring tip 180 at distal end 182. Positioning member 164 is secured to inner surface 172 of each coil 166 by either bonding or brazing. Unlike positioning member 34 shown in FIG. 1, however, distal end 182 of positioning member 164 extends distal to distal end 176 of coil member 162. Spring tip 180 of positioning member 164 enhances the ability of perfusion adaptor 160 to be self-guiding, i.e., capable of maneuvering independent of a separate guiding source.

Coil member 162 is preferably formed by winding a ribbon of a radiopaque metal, such as a platinum alloy, about a mandrel. The proximal and distal ends of the ribbon are secured to inner surface 172 of an adjacent coil by either bonding or brazing in order to make distal end 176 and proximal end 178 of coil member 162 relatively atraumatic.

Perfusion adaptor 160 has novel characteristics which permit perfusion adaptor 160 to accommodate a variety of intravascular conditions often encountered in the course of intravascular balloon catheter procedures. For instance, FIG. 10 shows a sectional view of artery 186 with balloon catheter 188 positioned across side branch 190 of artery 186. When a blockage of artery 186 occurs at an intersection of artery 186 and side branch 190, such as shown by lesion 192, inflation of balloon 194 occludes artery 186 and side branch 190.

FIG. 10A shows artery 106 of FIG. 10 with perfusion adaptor 160 between inflated balloon 194 and artery wall 196. As shown in FIG. 10A, coil member 162 is positioned adjacent balloon 194, with distal end 176 generally aligned with balloon distal end 198, and proximal end 178 generally aligned with balloon proximal end 200. With coil member 162 so positioned, flow path 174 is maintained despite the force applied to coil member 162 by balloon 194. Flow path 174 permits flow of blood past balloon 194 when it is inflated, thereby permitting balloon 194 to remain inflated within artery 186 for an extended period of time. In addition, spacings 168 of coil member 162 expose blood flowing through flow passage 174 to side branch 190, thereby allowing blood to flow generally transverse to flow path 174 and into side branch 190.

FIG. 10B is a sectional view of bend 202 of artery 186 showing perfusion adaptor 160 between inflated balloon 194 and artery wall 196. FIG. 10B shows additional novel and beneficial characteristics of coil member 162, which enables balloon 194 to adapt to a variety of intravascular conditions. Because of its spring-like effect, coil member 162 is capable of bending to accommodate tortuous curves of the vascular system. When balloon 194 must be inflated at bend 202 of artery 186, coil member 162 is able to bend to correspond to the shape of artery 186. The radial rigidity of coil member 162, however, preserves flow path 174 despite the force applied by balloon 194 against coil member 162. Thus, with coil member 162 positioned between balloon 194 and bend 202 of arterial wall 196, flow passage 174 continues to permit blood to flow past inflated balloon 194. In addition, in the unlikely event that proximal end 178 or distal end 176 of coil member 162 becomes occluded, blood can continue to flow through flow path 174 via spaces 168. Finally, like perfusion adaptor 30, perfusion adaptor 160 creates flow sinuses (shown in FIG. 3) through which blood can additionally flow when coil member 162 is positioned between arterial wall 196 and balloon 194.

Perfusion Adaptor 210 (FIG. 11)

FIG. 11 is a perspective view of perfusion adaptor 210 of the present invention. Perfusion adaptor 210 generally includes braided tube 212 and positioning member 214.

Braided tube 212 includes distal end 216, proximal end 218 and cylindrical opening 220, which extends from distal end 216 to proximal end 218. Braided tube 212 is formed by multiple strands of member 222, which are woven in a tubular "clothing weave." In preferred embodiments, member 222 is preferably a ribbon or a wire which is formed from a radiopaque material, such as a platinum alloy. The radiopacity of member 214 aids in the positioning perfusion adaptor 210, as has been previously discussed. Alternatively, member 222 can be formed of any suitable high strength polymer.

The clothing weave of members 222 provides radial strength to braided tube 212 sufficient to withstand the dilatation force from a balloon when braided tube 212 is positioned between an artery wall and an inflated balloon, as shown in FIGS. 2B, 3, 10A and 10B. In addition, the clothing weave of members 222 gives braided tube 212 axial flexibility, which enhances the trackability of braided tube 212 through tortuous curves of the vascular system. Furthermore, cylindrical opening 220 is able to permit a flow of blood past an inflated balloon in a manner similar to perfusion adaptor 30 shown in FIGS. 2B and 3. Finally, the clothing weave of members 222 provides spacings 224, which permits a transverse flow of blood relative to cylindrical opening 220 for side branch perfusion, similar to perfusion adaptor 140 of FIG. 8 and perfusion adaptor 160 of FIG. 9.

Positioning member 214 is attached to an inner surface of the clothing weave of members 222 by either bonding or brazing, as has been previously discussed. Alternatively, connection of positioning member 214 to braided tube 212 is enhanced by weaving distal portion 215 of positioning member 214 into the weave of members 222 and securing by bonding or brazing.

Perfusion Adaptor 230 (FIGS. 12-14)

FIG. 12 is a perspective view of perfusion adaptor 230 of the present invention. Perfusion adaptor 230 includes curved hollow member 232 and positioning member 234.

Curved hollow member 232 includes outer surface 236 and inner surface 238. Outer surface 236 and inner surface 238 are generally crescent-shaped to approximate the curve of inner artery wall 240 of artery 242 when perfusion adaptor 230 is positioned between inflated balloon 244 and inner artery wall 240 (shown in FIG. 13). Integrally formed within curved hollow member 232 at inner surface 238 are ribs 244 and 246. Ribs 244 and 246 extend from distal end 248 to proximal end 250 of curved hollow member 232. Ribs 244 and 246 trisect curved hollow member 232 to provide flow passages 252, 254 and 256. Flow passages 252, 254 and 256 each have a cross-sectional surface area ranging from about $8.5 \times 10^2$ square inches to about $3.8 \times 10^{-3}$ square inches, which permits a flow of blood past a balloon when perfusion adaptor 230 is inserted between inflated balloon 244 and artery wall 240, as shown in FIG. 13. Ribs 244 and 246 provide structural support to flow passages 252-256 sufficient to the withstand the dilatation force of balloon 244 when perfusion adaptor 230 is positioned between inflated balloon 244 and artery wall 240. In a preferred embodiment, curved hollow member 232 is formed by extrusion of a high molecular weight polymer, such as polyethylene.

Positioning member 234 is similar to positioning member 34 shown in FIG. 1. Positioning member 234 includes distal end 258, which is aligned with distal end 248 within flow passage 254, and is secured to upper inner surface 260 by bonding in the manner previously described. The method of using perfusion adaptor 230 is similar to described relative to FIGS. 2-2B and 4. As shown in FIG. 14, the arched construction of curved hollow member 232 provides adequate structural support to eliminate ribs 244 and 246, without sacrificing the integrity of flow passage 262.

Perfusion Adaptor 270 (FIGS. 15-16)

FIG. 15 shows a perspective view of perfusion adaptor 270 of the present invention. Perfusion adaptor 270 generally includes curved tubular array 272, sheath 274 and positioning member 276.

Curved tubular array 272 is comprised of a plurality of tubules 278. Each tubule 278 includes outer surface 280, inner surface 282 and lumen 284, which extends from distal end 286 to proximal end 288 of curved tubular array 272. Each lumen 284 has a cross-sectional surface area ranging from about $7.8 \times 10^{-5}$ square inches to about $2.0 \times 10^{-3}$ square inches. Tubules 278 are placed side-by-side in a curved array, as shown in FIGS. 15-16, with outer surfaces 280 of adjoining tubules 278 being bonded together with a suitable adhesive, such as epoxy. Each tubule 278 is made of a relatively rigid material, such as polyethylene, which insures that each lumen 284 will remain in an open position when curved tubular array 272 is positioned between an artery wall and an inflated balloon. Alternatively, curved tubular array 272 can be formed by an extrusion process.

In the preferred embodiment, tubules 278 of curved tubular array 272 are covered with flexible sheath 274, inner surface 285 of which is bonded to each outer surface 280 of tubules 278. Flexible sheath 274 is preferably made of silicone, which provides a lubricous, atraumatic covering to curved tubular array 272. Flexible sheath 274 thereby facilitates movement of curved tubular array 272 through a blood vessel.

Like curved hollow member 232 shown in FIG. 12, curved tubular array 272 provides means for permitting a flow of blood past an inflated balloon when curved tubular array 272 is positioned between an artery wall and an inflated balloon. Positioning member 276 is connected to curved tubular array 272 by inserting distal end 290 of positioning member 276 within lumen 284 of mediate tubule 292 and bonding it to inner surface 282 in a manner similar to that previously described. In addition, as shown in FIG. 16, curved tubular array 272 includes gaps 294 between adjacent tubules 278 and inner surface 285 of sheath 274, which are capable of allowing an additional flow of blood past tubules 278 when curved tubular array 272 is positioned between an artery wall and an inflated balloon.

Perfusion Adaptor 300 (FIGS. 17-20)

FIG. 17 is a perspective view of perfusion adaptor 300, which combines perfusion adaptor 30 of FIG. 1 within flexible sleeve 302 and permits perfusion adaptor 30 to be guided through a blood vessel along the shaft of a balloon catheter. Flexible sleeve 302 includes outer layer 304 and inner layer 306. Outer layer 304 includes outer surface 308 and inner surface 310, while inner layer 306 includes outer surface 312 and inner surface 314. As shown in FIG. 17, hollow member 32 of perfusion adaptor 30 is positioned between outer layer 304 and inner layer 306 near one side of flexible sleeve 302. Hollow member 32 is secured therein by bonding outer surface 42 of hollow member 32 to inner surface 310 of outer layer 304 and outer surface 312 of inner layer 306 with adhesive 316. Adhesive 316 further serves to connect outer surface 312 of inner layer 306 to the remainder of inner surface 310 of outer layer 304. Flexible sleeve 302 has an unexpanded outer and inner diameter which approximates the outer diameter of catheter shafts commonly used in intravascular balloon catheter procedures.

Figure 18:
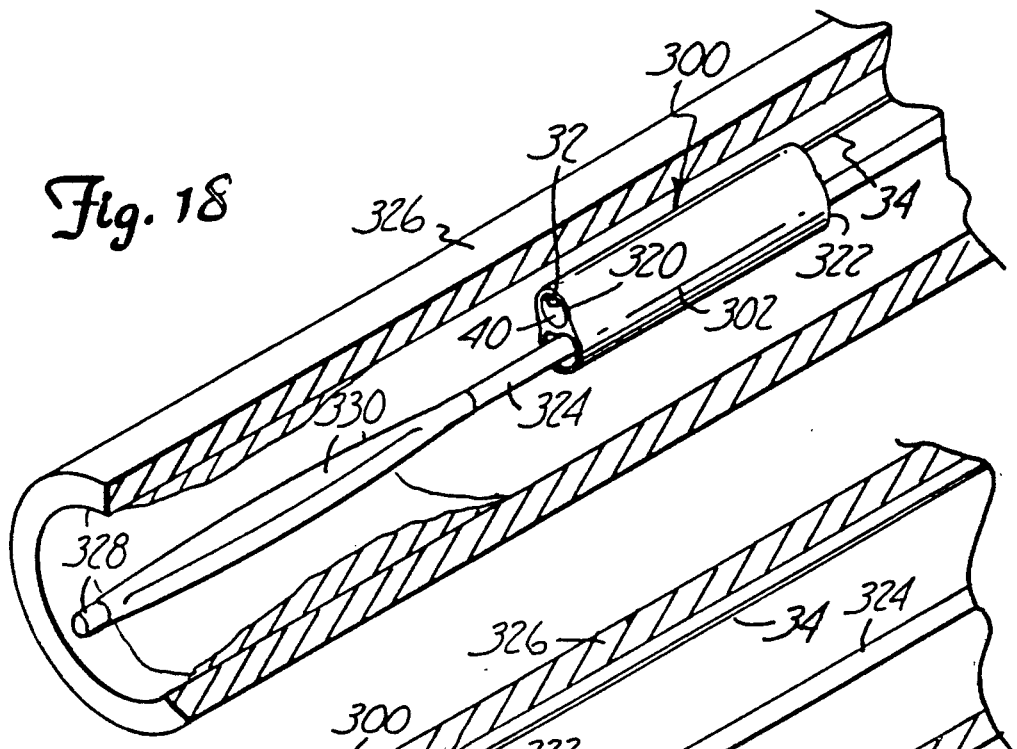
FIGS. 18-19 are perspective views of an artery with a section cut away demonstrating the method of using the adaptor of FIG. 17 with a balloon catheter.

Inner surface 314 of inner layer 306 defines opening 318, which extends from distal end 320 to proximal end 322 of flexible sleeve 302. As shown in FIG. 18, opening 318 is positioned over catheter shaft 324, which allows flexible sleeve 302 to guided over shaft 324 to balloon 300.

Figure 19:
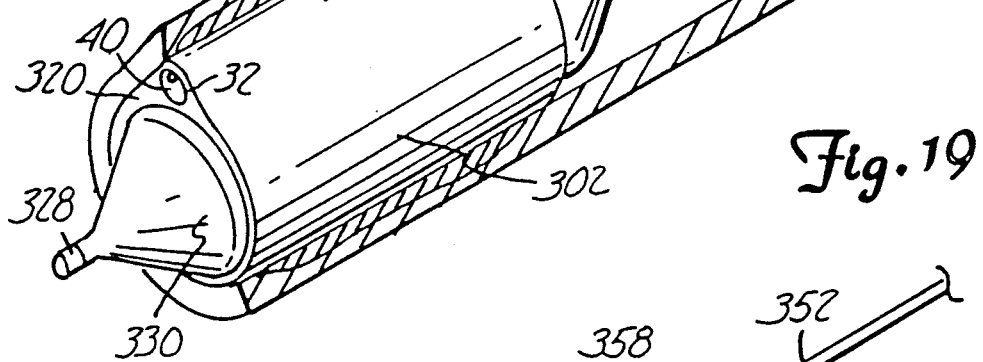

FIGS. 18 and 19 show one preferred method of positioning perfusion adaptor 30 within artery 326 when perfusion adaptor 30 is associated with flexible sheath 302. First, proximal end 322 of opening 336 is placed over distal end 328 of catheter shaft 324 prior to inserting catheter shaft 324 into artery 326. Perfusion adaptor 300 is then maintained proximal to balloon 330 (e.g., near a manifold of the catheter) until balloon 330 is properly positioned at the desired location within artery 326. In the event a flow of blood is desired or required past balloon 330, perfusion adaptor 300 can be advanced in a distal direction along catheter shaft 324 by applying longitudinal force to positioning member 34. The unexpanded inner and outer diameter of flexible sleeve 302 being relatively small, flexible sleeve 302 is able to advance through artery 326 with a relatively low profile.

With balloon 330 deflated, flexible sleeve 302 is advanced to and slid over balloon 330. Perfusion adaptor 300 is further advanced over balloon 330 until distal end 320 and proximal end 322 of flexible sleeve 302 generally are aligned with the distal and proximal ends of balloon 330, respectively. When balloon 330 is reinflated, flexible sleeve 302 expands to contact the wall of artery 326 with flow passage 40 of hollow member 32 allowing blood to flow past balloon 330 for as long as balloon 330 remains inflated within artery 326. In the event balloon 330 is being used for dilatation, flexible sleeve 302 is also capable of transmitting the dilatation force of balloon 330 to the wall of artery 326, to redilate artery 326.

Other method of loading perfusion adaptor 300 onto shaft 324 are also possible. For instance, when perfusion adaptor 300 is used with a catheter which has a removable manifold, perfusion adaptor 300 can be loaded onto shaft 324 after the catheter has been prepositioned within the artery.

While flexible sheath 302 shown in FIG. 17 is used in association with perfusion adaptor 30 shown in FIG. 1, flexible sheath 302 may also be used with other embodiments shown in FIGS. 6-9 and 11. As shown in FIG. 20, when flexible sheath 302 is used with an adaptor that is capable of side-branch perfusion, such as shown in FIGS. 8, 9 or 11, flexible sheath 302 includes openings 332 in outer surface 326 of outer layer 322. Openings 332 communicate with holes 146 shown in FIG. 8, spaces 168 shown in FIG. 9, or spaces 224 shown in FIG. 11, so as to permit blood to flow towards a side branch of an artery in the event sleeved perfusion adaptor 300 is so positioned.

In a preferred embodiment, flexible sleeve 302 is made of an elastic material, such as silicone. When sleeve 302 is made of a material other than silicone, inner surface 314 of inner layer 306 includes a lubricous coating, such as silicone, which enables flexible sleeve 302 to slide easily along shaft 324. Flexible sleeve 302 has a length which is less than or equal to perfusion adaptor 30. In one embodiment, the length of flexible sleeve 302 is substantially shorter than perfusion adaptor 30. Flexible sleeve preferably includes a mechanical stop which engages a proximal end of balloon 330 and prevents flexible sleeve 302 from being advanced past balloon 330.

Figure 21:
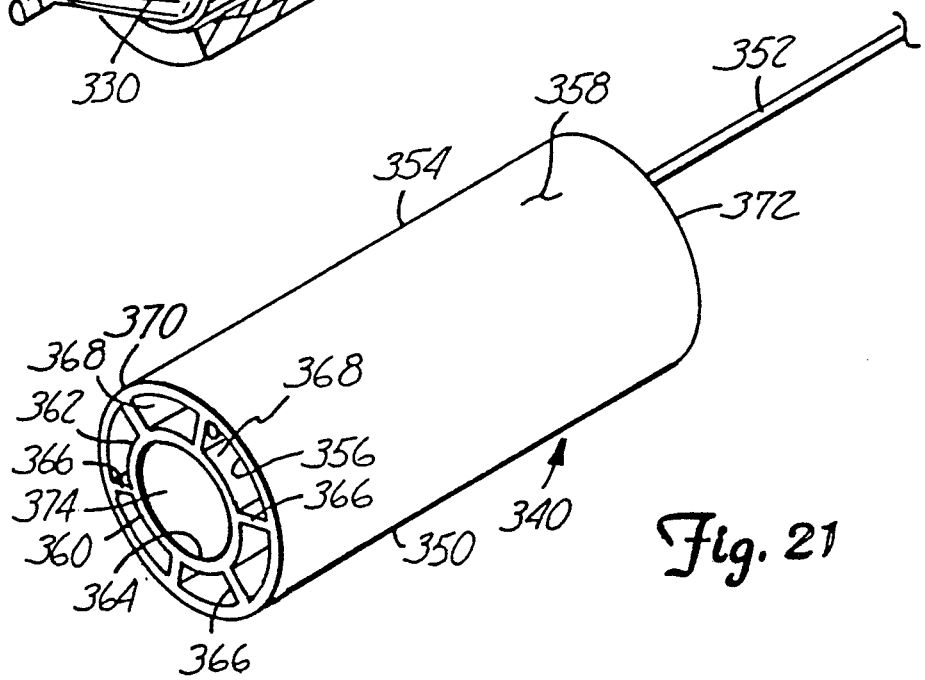
FIG. 21 is a perspective view of a tenth embodiment of the adaptor of the present invention.

Perfusion Adaptor 340 (FIGS. 21 and 23)

FIG. 21 is a perspective view of perfusion adaptor 340 of the present invention. As shown in FIG. 21, perfusion adaptor 340 generally includes ductal sleeve 350 and positioning member 352.

Ductal sleeve 350 is comprised of outer membrane 354, which has inner surface 356 and outer surface 358, and inner membrane 360, which has outer surface 362 and inner surface 364. Inner membrane 360, which has an inner and an outer diameter smaller than an inner and outer diameter of outer membrane 354, is coaxially positioned within outer membrane 354. A plurality of radially spaced ribs 366 are integrally formed between outer surface 362 of inner membrane 360 and inner surface 356 of outer membrane 354, thereby creating a plurality of ducts 368. Ducts 368 extend from distal end 370 to proximal end 372 of ductal sleeve 350. Each duct 368 has a cross-sectional surface area ranging from about $8.6 \times 10^{-5}$ square inches to about $3.8 \times 10^{-3}$ square inches.

Inner surface 364 of inner membrane 360 defines sleeved opening 374 which, like sleeved opening 318 shown in FIG. 17, is sized to be positioned over and advanced along a catheter shaft.

Positioning member 352 is positioned within any duct 368 and secured therein by bonding according to the manner previously described in previous embodiments. By applying an appropriate longitudinal force to positioning member 352, ductal sleeve 350 is longitudinally movable along a catheter shaft while the catheter shaft is positioned within an artery.

Ductal sleeve 350 is generally used with a catheter in a manner similar to that described relative to FIGS. 18 and 19. As shown in FIG. 22, with ductal sleeve 350 positioned over balloon 378, ducts 368 lie between balloon 378 and wall 380 of artery 382. With balloon 378 inflated within ductal sleeve 350, ribs 366 provide sufficient structural support between outer membrane 354 and inner membrane 360 to insure that ducts 368 remain open so as to permit a flow of blood past balloon 378 for as long as balloon 378 and ductal sleeve 350 remain within artery 382.

Ductal sleeve 350 has an inner and outer diameter which closely approximates an outer diameter of a variety of catheter shafts commonly used in intravascular balloon catheter procedures. In one preferred embodiment, ductal sleeve 350 is made of a flexible material, such as silicone, which enables outer membrane 354 and inner membrane 360 to expand as balloon 378 is inflated. This allows outer surface 358 of outer membrane 354 to transmit the dilatation force of balloon 378 to wall 380 of artery 382 when balloon 378 is inflated. Ductal sleeve 350 has a length which is generally equal to or greater than that of balloons used in the art.

In an alternative embodiment, shown in FIG. 23, outer membrane 354 includes a plurality of openings 386 along outer surface 358, which communicate with ducts 368. Openings 386, each of which has a diameter ranging from about 0.015 to about 0.050 inches, expose a transverse flow path for blood passing through ducts 368 when ductal sleeve 350 is positioned within artery 382 across a side branch (not shown) of artery 382 (as generally shown in FIG. 10).

Perfusion Adaptor 390 (FIGS. 24–26)

FIG. 24 shows a perspective view of perfusion adaptor 390 of the present invention. Perfusion adaptor 390 generally includes perfusion sleeve 392 and positioning member 394. Perfusion sleeve 392 is generally tubular-shaped and includes outer surface 396 and inner surface 398. Outer surface 396 is relatively smooth, while inner surface 398 is corrugated-like. Inner surface 398 includes a plurality of radially spaced ridges 400 and grooves 402, which extend from distal end 404 to proximal end 406 of perfusion sleeve 392. Each ridge 400 includes perfusion passage 408, which enables blood to flow from proximal end 406 to distal end 404 of perfusion sleeve 392 when perfusion sleeve 392 is positioned over inflated balloon 412 within artery 415 (shown in FIG. 25).

Perfusion sleeve 392 further includes sleeve opening 410, which permits perfusion sleeve 392 to be positioned over a catheter shaft and used in a manner similar to that described relative to FIGS. 18 and 19. Positioning member 394 lies within sleeve opening 410 and is bonded within groove 402 in a manner described in previous embodiments.

FIG. 25 is a partial perspective view of artery 415 with a section cut away showing perfusion sleeve 392 positioned over balloon 412 between balloon 412 and wall 413 of the artery 415. As shown in FIG. 25, when perfusion sleeve 392 is positioned over inflated balloon 412, proximal end 406 and distal end 404 are generally aligned with proximal and distal ends, respectively, of balloon 412. So positioned, perfusion passages 40B permit blood to flow past balloon 412 for as long as balloon 412 remains inflated within artery 415. Outer surface 396 of perfusion sleeve 392 is made of an elastic material, such as silicone which enables outer surface 396 to expand and transmit the dilatation force of balloon 412 to wall 413 of artery 415 when balloon 412 is inflated within artery 415.

FIG. 26 is a sectional view of balloon 412 and perfusion sleeve 392 taken along line 26—26 of FIG. 25. As shown in FIG. 26, with balloon 412 inflated within sleeve opening 410, outer surface 416 of balloon 412 contacts ridges 400 of inner surface 398 of perfusion sleeve 392. During inflation of balloon 412, however, outer surface 416 of balloon 412 is unable to completely conform to inner surface 398 of perfusion sleeve 392. Thus, grooves 402 interact with outer surface 416 of balloon 412 to form additional flow passages 418 along grooves 402. Flow passages 418, like perfusion passages 408, permit a flow of blood past balloon 412 when balloon 412 is inflated within perfusion sleeve 392.

Perfusion Adaptor 420 (FIGS. 27–29)

FIG. 27 is a perspective view of a twelfth embodiment of perfusion adaptor 420 of the present invention. Perfusion adaptor 420 generally includes sleeve 422, tubules 424 and positioning member 426.

Sleeve 422 is a thin, open-ended tube of flexible material, such as silicone, which includes outer surface 428 and inner surface 430. Sleeve 422 has an inner and outer diameter in an unexpanded state which permits sleeve 422 to fit over a catheter shaft, as has been described relative to FIGS. 18 and 19.

Tubules 424 each include outer surface 432, inner surface 434 and flow passages 436, which extend from distal end 438 to proximal end 440 of perfusion adaptor 420. Each flow passage 436 has an inner diameter which ranges from about 0.010 to about 0.050 inches. Tubules 424 are radially spaced about inner surface 430 of sleeve 422 and secured by bonding outer surface 432 of tubules 424 to inner surface 430 with a suitable adhesive, such as RTV silicone. Flow passages 436 provide a means for blood to flow from proximal end 440 to distal end 438 of perfusion adaptor 420 when perfusion adaptor 420 is positioned over balloon 442, as shown in FIGS. 28-29. A portion of each outer surface 432 of tubules 424, which is oriented toward a longitudinal axis of perfusion adaptor 420, defines contact surface 444. Contact surfaces 444 of tubules 424 collectively define an effective inner diameter of sleeve 422. The effective inner diameter of sleeve 422 is large enough to permit perfusion adaptor 420 to be positioned over and slid along a catheter shaft, as similarly shown in FIGS. 18-19.

In one preferred embodiment, positioning member 426 is secured to inner surface 430 of sleeve 422 between adjacent tubules 424 and bonded therein in a manner described in previous embodiments. In an alternative embodiment, positioning member 426 is inserted within any tubule 424 and bonded therein.

As shown in FIGS. 28 and 29, perfusion adaptor 420 is guided over catheter shaft 446 and is positioned over balloon 442. With perfusion adaptor 420 positioned over balloon 442, inflation of balloon 442 causes outer surface 448 of balloon 442 to engage contact surface 444 of tubules 424 and radially expand sleeve 422. Due to the elastic nature of sleeve 422, outer surface 428 of sleeve 422 contacts and transmits the dilatation force of balloon 442 to wall 450 of artery 452. With outer surface 428 of sleeve 422 contacting wall 450 of artery 452, balloon 442 and perfusion adaptor 420 are able to remain within and maintain an outward pressure on artery wall 450 for an extended period of time.

As further shown in FIGS. 28-29, tubules 424 have sufficient rigidity to withstand the inflation pressure of balloon 442 and permit a flow of blood through flow passages 436. In addition, spaces 454 between adjacent tubules 424 are created due to the interaction of outer surface 448 of balloon 442, outer surfaces 432 of tubules 424 and inner surface 430 of sleeve 422. Spaces 454 permit additional flow space for blood to flow past balloon 442 when perfusion adaptor 420 is positioned over balloon 442 between balloon 442 and artery wall 450. Perfusion adaptor 420 therefore enables balloon 442 to remain inflated within artery for extended periods of time while allowing blood flow past the inflated balloon.

Compliancy Adaptor 458 (FIGS. 30–32)

FIG. 30 is a perspective view of the compliancy adaptor 458 of the present invention, which generally includes sleeve 460 and positioning member 462. As shown in FIG. 30, sleeve 460 is generally tubular-shaped, with outer surface 464, inner surface 466 and central opening 468, which extends from distal end 470 to proximal end 472 of sleeve 460. Sleeve 460 is extruded from a relatively noncompliant polymer material, such as polyethylene terephthalate (PET). In preferred embodiments, the distance between outer surface 464 and inner surface 466 is about $0.5 \times 10^{-3}$ to about $5.0 \times 10^{-3}$ inches. Central opening 468 permits sleeve 460 to be positioned over a shaft of a dilatation balloon catheter in a manner similar to that discussed relative to FIGS. 18-19.

Positioning member 462 is inserted within central opening 468 and bonded to inner surface 466 with an appropriate adhesive as has been previously discussed in previous embodiments. In one embodiment, shown in FIG. 31A, positioning member 462 is bonded to inner surface 468 along first side 476. In an alternative embodiment, shown in FIG. 31B, positioning member 462 is bonded to inner surface 466 along second side 478. As shown in FIGS. 31A-31B, first side 476 has a length greater than second side 478 such that distal end 470 and proximal end 472 are angled from first side 476 to second side 478. The angling of distal end 470 and proximal end 472 enhances the trackability of sleeve 460 as it is moved over a catheter shaft through a vessel of the vascular system.

Like the embodiments shown in FIGS. 17-29, sleeve 460 is designed to move along catheter shaft 480 and fit over balloon 482 of dilatation balloon catheter 484, with proximal end 472 and distal end 470 generally aligned with a proximal and distal end of balloon 482, respectively. As in the previous embodiments, sleeve 460 is guided over catheter shaft 480 to deflated balloon 482 by applying an appropriate longitudinal force to positioning member 462. As shown in FIG. 32, with sleeve 460 positioned over balloon 482, balloon 482 is inflated to engage inner surface 466 of sleeve 460. The positioning of sleeve 460 over balloon 482 is performable prior to insertion of balloon 482 within an artery, as shown in FIG. 32. Alternatively, sleeve 460 is positionable over balloon 482 after balloon 482 has been prepositioned within an artery in a manner similar to that described relative to FIGS. 18-19. Sleeve 460 limits the inflated outer diameter of balloon 482 and provides a simple and inexpensive way of controlling the radial size and enhancing the strength of balloon 482 during inflation, especially when balloon 482 is made of a compliant material. Sleeve 460 has an outer and inner diameter which is sized according to the particular artery size being treated.

The following tables contain data obtained during inflation tests performed on various sized standard polyolefin copolymer balloons which were covered by a noncompliant sleeve, such as sleeve 460. The outer diameter rating of the noncompliant sleeve was determined according to the outer diameter of a balloon made of the same noncompliant material as the noncompliant sleeve at between 7 to 10 atmospheres of inflation pressure. The sleeve-covered balloons were immersed in the 37° C. water bath and inflated by increasing fluid pressure within the balloons by increments of 1 atmosphere. Beginning at 4 atmospheres, each incremental pressure level was maintained for 15 seconds, during which the outer diameter of each sleeved balloon was measured by micrometry. The incremental inflation pressure increases were continued until the balloon failed. As reflected in the following tables, the rate of radial expansion and burst rate of the sleeve-covered balloons were then compared to similar data obtained for similar balloons which were not covered by a noncompliant sleeve of the present invention.

The first column of each table indicates fluid pressure in atmospheres. The second column of each table indicates the outer diameter measurements in millimeters of the balloon alone. The third column indicates the outer diameter measurements, also in millimeters, of sleeve 460 which covered a balloon similar to the balloon in column 2. The fourth column indicates the difference in millimeters between the outer diameter of the balloon of column 2 and the outer diameter of the sleeve-covered balloon of column 3.

Test No. 1

Test No. 1 was conducted with balloons having an outer diameter rating of 3.0 millimeters at a pressure of eight atmospheres and a noncompliant sleeve having an outer diameter rating also of 3.0 millimeters. The sleeve completely covered the balloon from its proximal shaft bonding region to its distal shaft bonding region. The following test data was obtained:

TABLE 1

| Pressure (ATM) | Balloon Outer Diameter (mm) | Sleeve/Balloon Outer Diameter (mm) | Outer Diameter Differential (mm) |
| --- | --- | --- | --- |
| 4 | 2.68 | 2.77 | −0.09 |
| 5 | 2.76 | 2.86 | −0.10 |
| 6 | 2.84 | 2.90 | −0.06 |
| 7 | 2.92 | 2.91 | +0.10 |
| 8 | 3.00 | 2.92 | +0.08 |
| 9 | 3.08 | 2.94 | +0.14 |
| 10 | 3.16 | 2.96 | +0.20 |
| 11 | 3.24 | 2.97 | +0.27 |
| 12 | 3.32 | 2.98 | +0.34 |
| 13 | Burst | 3.00 | |
| 14 | | 3.00 | |
| 15 | | 3.01 | |
| 16 | | 3.02 | |
| 17 | | 3.03 | |
| 18 | | 3.04 | |
| 19 | | Burst | |

The results of Test No. 1 show *five* beneficial effects of the use on a non-compliant sleeve, such as sleeve 460, with an ordinary compliant balloon. First, as shown in Table 1, the outer diameter of the ordinary balloon increased from its rated size of 3.00 millimeters at 8 atmospheres to 3.32 millimeters at 12 atmospheres, which reflects a 9.6% increase in diameter. By comparison, through the same pressure range, the diameter of the sleeve-covered balloon increased only 2.0%. Moreover, from 6 atmospheres to 18 atmospheres, the outer diameter of the sleeve-covered balloon increased only 4.6%. Most importantly, however, the diameter of the sleeve-covered balloon increased only 1.3% greater than the rated diameter (3.0 mm) of the sleeve.

Second, by comparing the diameter of the sleeve-covered balloon (col. 3) with the uncovered balloon (col. 2) at 8 atmospheres of pressure, the results of Test 1 also show that the noncompliant sleeve of the present invention is capable of reducing or downsizing the outer diameter of a particular balloon while still being able to safely achieve the balloon's rated size (3.0 mm) at inflation pressures of between 13 and 14 atmospheres.

Third, the relatively low percent increase in the outer diameter of the sleeve-covered balloon correlates to a relatively slow diameter increase rate. The diameter of the sleeve-covered balloon steadily increased by only about 0.01 millimeter per incremental increase in inflation pressure. By comparison, the outer diameter of the uncovered balloon, as shown in column 2, increased 0.08 millimeters per incremental increase in inflation pressure. The relatively steady increase in diameter of the sleeve-covered balloon over the relatively large pressure range enables a physician to more accurately control the dilatation of the blood vessel.

Fourth, the uncovered balloon failed at about 13 atmospheres, while the sleeve-covered balloon failed at about 19 atmospheres. The use of a noncompliant sleeve of the present invention, therefore, accounted for about a 46.1% increase in the burst pressure of the balloon.

Finally, failure of the balloon, which occurred in the balloon body, did not affect the integrity of the non-compliant sleeve, with the balloon failure contained within the sleeve. Use of noncompliant sleeve 460 therefore offers an ability to not only increase the burst pressure of a balloon (and hence, the safety margin of balloon failure), but sleeve 460 is also able to protect the wall of an artery by containing the balloon burst within the inner dimensions of the sleeve.

Test No. 2

Test No. 2 was conducted with balloons having an outer diameter rating of 2.0 millimeters at a pressure of eight atmospheres and a sleeve having an outer diameter rating of 2.25 millimeters. With the sleeve covering only the inflatable portion of the balloon, the following test data was obtained:

TABLE 2

| Pressure (ATM) | Balloon Outer Diameter (mm) | Sleeve/Balloon Outer Diameter (mm) | Outer Diameter Differential (mm) |
|---|---|---|---|
| 4 | 1.78 | 2.01 | −.23 |
| 5 | 1.84 | 2.05 | −.21 |
| 6 | 1.89 | 2.07 | −.18 |
| 7 | 1.95 | 2.10 | −.15 |
| 8 | 2.00 | 2.12 | −.12 |
| 9 | 2.06 | 2.15 | −.09 |
| 10 | 2.11 | 2.19 | −.08 |
| 11 | 2.17 | 2.20 | −.03 |
| 12 | 2.22 | 2.23 | −.01 |
| 13 | 2.28 | 2.25 | +.03 |
| 14 | 2.33 | 2.25 | +.08 |
| 15 | Burst | 2.26 | |
| 16 | | 2.28 | |
| 17 | | Burst | |

The results of Test No. 2 established beneficial effects of sleeve 460 similar to those mentioned relative to Test No. 1. First, as shown in column 2, the outer diameter of the ordinary balloon increased from its rated size of 2.00 millimeters to 2.33 millimeters before failing, which reflects a 14.2% increase in diameter. By comparison, the sleeve covered balloon increased from 2.01 millimeters at 4 atmospheres to 2.28 millimeters at 16 atmospheres, which reflects only an 11.8% increase. More importantly, the diameter of the sleeve covered balloon increased only about 1.3% above the rated diameter (2.25 millimeters) of the sleeve.

Second, a comparison of the diameters of the sleeve covered balloon (col. 3) with the uncovered balloon (col. 2) indicates that by using a sleeve with an outer diameter which is slightly larger than the rated size of the balloon, the non-compliant sleeve of the present invention is capable of increasing or upsizing the outer diameter of the balloon at inflation pressures of between 4 and about 12 atmospheres. This allows a sleeve-covered balloon to achieve a desired outer diameters near the balloon's rated diameter at lower inflation pressures, which increases the margin of safety of balloon failure.

Finally, the sleeve-covered balloon failed at about 17 atmospheres while the uncovered balloon failed at about 15 atmospheres. The burst pressure of the sleeve-covered balloon therefore increased about 13.3% over the uncovered balloon, which indicates an increase in the safety margin of balloon failure. In particular, prior to balloon failure, the proximal end of the balloon distended at about 14 atmospheres, likely due to the reduced area of coverage of sleeve 460 with the balloon. Balloon failure then occurred at proximal end of the balloon.

Test No. 3

Test No. 3 was conducted with balloons having an outer diameter rating of 2.0 millimeters at a pressure of six atmospheres and a sleeve having an outer diameter rating of 2.25 millimeters. With the sleeve covering only the inflatable portion of the balloon, like Test No. 2, the following test data was obtained:

TABLE 3

| Pressure (ATM) | Balloon Outer Diameter (mm) | Sleeve/Balloon Outer Diameter (mm) | Outer Diameter Differential (mm) |
|---|---|---|---|
| 4 | 1.86 | 2.02 | −.16 |
| 5 | 1.93 | 2.08 | −.16 |
| 6 | 2.00 | 2.13 | −.13 |
| 7 | 2.07 | 2.17 | −.10 |
| 8 | 2.14 | 2.20 | −.06 |
| 9 | 2.21 | 2.23 | −.02 |
| 10 | 2.28 | 2.25 | +.03 |
| 11 | 2.35 | 2.25 | +.10 |
| 12 | 2.42 | 2.26 | +.16 |
| 13 | 2.49 | 2.28 | +.21 |
| 14 | Burst | 2.28 | |
| 15 | | 2.30 | |
| 15.5 | | 2.31 | |
| 16 | | Burst | |

The results of Test No. 3 were similar to those obtained from Test No. 2. First, the balloon increased in radial size from its rated size of 2.00 millimeters to 2.49 millimeters, which reflects an increase of 19.7%. By comparison, the sleeve-covered balloon increased from 2.02 millimeters at 4 atmospheres to 2.31 millimeters at 15.5 atmospheres, which reflects an increase of only about 12.6%. More importantly, the increase of the sleeve covered balloon to 2.31 millimeters reflects only a 2.7% increase over the rated diameter of the noncompliant sleeve.

The burst pressure of the sleeve-covered balloon increased to about 16 atmospheres as compared with about 14 atmospheres of the uncovered balloon, which reflects about a 14.3% increase in the burst pressure of the ordinary balloon. The balloon failure occurred in the proximal cone area of the balloon, an area which was not covered by the non-compliant sleeve.

Test No. 4

Test No. 4 was conducted with balloons having an outer diameter rating of 2.0 millimeters at a pressure of six atmospheres and a sleeve having an outer diameter rating of 2.25 millimeters. With the sleeve covering only the inflatable portion of the balloon, like Tests No. 2 and 3, the following data was obtained:

TABLE 4

| Pressure (ATM) | Balloon Outer Diameter (mm) | Sleeve/Balloon Outer Diameter (mm) | Outer Diameter Differential (mm) |
|---|---|---|---|
| 4 | 1.86 | 2.01 | −.15 |
| 5 | 1.93 | 2.07 | −.14 |
| 6 | 2.00 | 2.12 | −.12 |
| 7 | 2.07 | 2.16 | −.09 |
| 8 | 2.14 | 2.19 | −.05 |
| 9 | 2.21 | 2.23 | −.02 |
| 10 | 2.28 | 2.24 | +.04 |
| 11 | 2.35 | 2.26 | +.09 |
| 12 | 2.42 | 2.27 | +.16 |
| 13 | 2.49 | 2.29 | +.20 |

TABLE 4-continued

| Pressure (ATM) | Balloon Outer Diameter (mm) | Sleeve/Balloon Outer Diameter (mm) | Outer Diameter Differential (mm) |
|---|---|---|---|
| 14 | Burst | 2.29 | |
| 15 | | 2.30 | |
| 16 | | 2.31 | |
| 17 | | Burst | |

The results of Test No. 4 are similar to those obtained from Tests No. 2 and 3, except that the balloon failure occurred at the distal bond between the balloon and the catheter shaft, an area which was not covered by the sleeve. Failure of the balloon did not damage the integrity of the sleeve.

Test No 5

Test No. 5 was conducted with balloons having an outer diameter rating of 2.5 millimeters at a pressure of six atmospheres with a sleeve also having an outer diameter rating of 2.5 millimeters. With the sleeve covering only the inflatable portion of the balloon, like Test Nos. 2–4, the following test data was obtained:

TABLE 5

| Pressure (ATM) | Balloon Outer Diameter (mm) | Sleeve/Balloon Outer Diameter (mm) | Outer Diameter Differential (mm) |
|---|---|---|---|
| 4 | 2.32 | 2.41 | −.085 |
| 5 | 2.41 | 2.43 | −.02 |
| 6 | 2.5 | 2.46 | +.04 |
| 7 | 2.59 | 2.46 | +.13 |
| 8 | 2.68 | 2.47 | +.21 |
| 9 | 2.76 | 2.48 | +.28 |
| 10 | 2.85 | 2.48 | +.37 |
| 11 | 2.94 | 2.49 | +.45 |
| 12 | 3.03 | 2.50 | +.47 |
| 13 | 3.11 | 2.50 | +.61 |
| 14 | Burst | 2.51 | |
| 15 | | 2.51 | |
| 16 | | 2.52 | |
| 17 | | 2.53 | |
| 18 | | Burst | |

As in Tests Nos. 1–4, the results of Test No. 5 indicate that the outer diameter of the sleeve-covered balloon remained relatively close to the rated diameter of the sleeve during inflation of the balloon, while the outer diameter of the uncovered balloon increased substantially above the balloon's rated diameter. The balloon increased from 2.5 millimeters to about 3.11 millimeters before failing, which reflects about a 19.6% increase in diameter. The sleeve-covered balloon, on the other hand, increased from 2.41 millimeters to about 2.53 millimeters, which reflects about a 4.7% increase in size of the sleeve-covered balloon. More importantly, however, the sleeve-covered balloon increase to 2.53 millimeters at 17 atmospheres of pressure was only about 1.2% above the rated outer diameter of the sleeve (2.5 mm).

Balloon failure of the uncovered balloon occurred at about 14 atmospheres, while failure of the sleeve-covered balloon occurred at about 18 atmospheres. The use of sleeve 460 therefore accounted for about a 28.6% increase in the burst pressure of the balloon.

Similar to the test results achieved in Test No. 1, Test No. 5 indicates that use of a non-compliant sleeve having an outer diameter which closely approximates the rated outer diameter of a balloon effectively reduces the outer diameter of the balloon through lower inflation pressures (4 atmospheres through 11 atmospheres) while still being able to safely achieve the balloons rated size (2.5 millimeters) at inflation pressures of between about 12 and 13 atmospheres.

Tables 6 and 7 below summarize some of the more significant beneficial effects of using a noncompliant sleeve of the present invention with a compliant balloon:

TABLE 6

| Test # | Rated Sleeve Size (mm) | Maximum Measured Sleeve Size (mm) | % Diameter Increase Over Rated Diameter |
|---|---|---|---|
| | 3.0 | 3.04 | 1.3% |
| 2 | 2.25 | 2.28 | 1.3% |
| 3 | 2.25 | 2.31 | 2.7% |
| 4 | 2.25 | 2.31 | 2.7% |
| 5 | 2.5 | 2.53 | 1.2% |
| Average | | | 1.84% |

TABLE 7

| Test # | Burst Pressure Without Sleeve (ATM) | Burst Pressure With Sleeve (ATM) | % Burst Pressure Increase |
|---|---|---|---|
| 1 | 13 | 19 | 46.1% |
| 2 | 15 | 17 | 13.3% |
| 3 | 14 | 16 | 14.3% |
| 4 | 14 | 17 | 21.4% |
| 5 | 14 | 18 | 28.6% |
| Average | | | 24.7% |

CONCLUSION

A variety of adaptors have been disclosed which are operable with intravascular balloon catheters typically used for intravascular balloon procedures, to modify a balloon of the balloon catheter when a desired performance, beyond the capability of the balloon, is desired. Essentially, the adaptor includes a hollow member and an elongated positioning member, which is connected to the hollow member for moving the hollow member within a blood vessel. With the balloon catheter positioned within the blood vessel, the adaptor is capable of longitudinal movement through the blood vessel, between the balloon catheter and a wall of the blood vessel, independent of the balloon catheter. The hollow member is maneuvered adjacent to the balloon by manipulating the positioning member. Inflation of the balloon secures the hollow member against the balloon in such a manner that the properties of the hollow member are imparted to the balloon.

It is intended within the scope of this disclosure that features discussed relative to one embodiment of the adaptor are equally applicable to each of the other embodiments.

Embodiments of the adaptor shown in FIGS. 1–29 create perfusion passages past a variety of balloon designs in a variety of intravascular conditions, when the adaptor is secured to a surface of the inflated balloon. When the balloon is positioned across a side branch of the blood vessel, the perfusion passages of some embodiments of the adaptor are exposed in a manner which permits blood to flow transverse to the perfusion passages into the side branches. Alternatively, when the balloon is inflated in a bend of the blood vessel, some embodiments of the adaptor readily conform to the bend while maintaining the perfusion passage.

The embodiment of the adaptor shown in FIGS. 30-32 is a sleeve made of a material which envelops a balloon to restrict its radial size, enhance its strength and protect the blood vessel in the event of balloon failure. In addition, the sleeve enables a physician to resize the balloon to suite the artery size encountered during an intravascular balloon catheter procedure without a complete catheter exchange. Although the sleeve has been described as being made of a material having reduced compliance, other materials of a more compliant nature can be substituted to achieve the desired performance of balloon strength enhancement, blood vessel protection, and/or balloon resizing. This is accomplished by varying the wall thickness of the sleeve according to the desired result sought to be obtained.

The use of an adaptor which has the abilities disclosed in the aforementioned embodiments allows a physician to use a single, ordinary balloon catheter which has a relatively low crossing profile to perform an intravascular procedure, yet still be able to easily and inexpensively obtain balloon characteristics required or desired for the intravascular condition encountered. Moreover, use of an adaptor of the present invention advantageously achieves the required or desired balloon characteristics relatively quickly, as compared to a complete catheter exchange.

The adaptors of the present invention are guided through a blood vessel three alternative ways: First, some embodiments of the adaptor are self-guided through the blood vessel, with a radiopaque marker aiding in the positioning of the adaptor. Second, when used with a balloon catheter which has a guide wire external the shaft of the catheter, some embodiments of the adaptor are capable of being positioned over and slid along the guide wire to the balloon. Finally, some embodiments of the adaptor include a sleeve which enables the adaptor to be positioned over and slid along the catheter shaft to the balloon.

Although the present invention has been described with reference to preferred embodiments, workers skilled in the art will recognize that changes may be made in form and detail without departing from the spirit and scope of the invention.

What is claimed is:

1. An intravascular balloon catheter system, the balloon catheter system comprising:
   a catheter shaft having a proximal end, a distal end, an outer surface and at least one lumen extending between the proximal end and the distal end;
   an inflatable balloon connected to the shaft at the distal end of the shaft; and
   adaptor means independently movable relative to and operable with the balloon, for modifying a performance of the balloon, when the balloon is inflated within the blood vessel.

2. The balloon catheter system of claim 1 wherein the adaptor means further comprises:
   a hollow member having a proximal end, a distal end, an outer surface, an inner surface and an opening between the proximal and distal ends; and
   positioning means connected to the hollow member, for longitudinally moving the hollow member within the blood vessel, between a wall of the blood vessel and the shaft of the catheter, and for positioning the hollow member so as to contact a surface of the balloon and effect the modified performance of the balloon.

3. The balloon catheter system of claim 2 wherein inflating the balloon secures the hollow member between the wall of the blood vessel and an outer surface of the balloon, with the proximal end and the distal end of the hollow member exposed at a proximal end and a distal end of the balloon.

4. The balloon catheter system of claim 3 wherein the opening is positioned between the balloon and the wall of the blood vessel when the balloon is inflated.

5. The balloon catheter system of claim 4 wherein the opening establishes a flow path for blood past the balloon when the balloon is inflated within the blood vessel.

6. The balloon catheter system of claim 5 wherein the opening is defined by the inner surface of the hollow member.

7. The balloon catheter system of claim 6 wherein the outer surface of the hollow member contacts the blood vessel wall and the outer balloon surface along a contact zone.

8. The balloon catheter system of claim 7 wherein inflating the balloon further creates spaces adjacent the contact zone, between the outer surface of the hollow member and the wall of the blood vessel, the spaces permitting a flow of blood past the balloon while the balloon is inflated within the blood vessel.

9. The balloon catheter system of claim 7 and further comprising:
   exposure means through a side wall hollow member for exposing the opening so as to permit a flow of blood transverse to the opening, the flow of blood through the exposure means capable of feeding a side branch of the artery when the balloon and hollow member are positioned across the side branch.

10. The balloon catheter system of claim 9 wherein the exposure means includes a plurality of holes.

11. The balloon catheter system of claim 9 wherein the hollow member comprises a tubular coil of a flat member, and wherein the exposure means comprises spaces between adjacent coils of the hollow member.

12. The balloon catheter system of claim 11 wherein the flat member is a metal member.

13. The balloon catheter system of claim 12 wherein the metal member is radiopaque.

14. The balloon catheter system of claim 11 wherein the flat member is a polymer.

15. The balloon catheter system of claim 9 wherein the hollow member comprises a tubular braid of a wire-like member, and wherein the exposure means comprises gaps between an intersection of the wire like members.

16. The balloon catheter system of claim 4 wherein inflation of the balloon causes the outer surface of the hollow member to contact the wall of the artery, and the inner surface of the hollow member to contact the outer surface of the balloon.

17. The balloon catheter system of claim 16 wherein inflation of the balloon further causes the inner and outer surfaces of the hollow member to expand.

18. The balloon catheter system of claim 17 wherein the opening is defined between the inner surface and the outer surface of the hollow member, and wherein the opening is maintained, when the balloon is inflated within the blood vessel, to permit a flow of blood past the inflated balloon.

19. The balloon catheter system of claim 18 and further comprising:

exposure means through the outer surface of the hollow member for exposing the opening so as to permit a flow of blood transverse to the opening, the flow of blood through the exposure means capable of feeding a side branch of the artery when the balloon and adaptor are positioned across the side branch.

20. The balloon catheter system of claim 19 wherein the exposure means includes a plurality of holes.

21. The balloon catheter system of claim 16 wherein the opening is defined by the inner surface of the hollow member.

22. The balloon catheter system of claim 4 wherein the opening of the hollow member has a predetermined diameter larger than the balloon when the balloon is deflated.

23. The balloon catheter system of claim 22 wherein the hollow member is positionable with respect to the balloon so that the balloon can be positioned within the opening of the hollow member.

24. The balloon catheter system of claim 23 wherein the hollow member is made of a material other than a material of the balloon.

25. The balloon catheter system of claim 24 wherein an outward radial expansion of the balloon is restricted to the predetermined diameter of the hollow member when the balloon is inflated.

26. The balloon catheter system of claim 25 wherein the predetermined diameter of the hollow member increases less than about 2.7% when the balloon is inflated.

27. The balloon catheter system of claim 26 wherein the material of the hollow member has a characteristic so that positioning the hollow member over the balloon increases a pressure tolerance of the balloon between about 12.5% and about 33.3%.

28. The balloon catheter system of claim 27 wherein the proximal end and the distal end of the hollow member are angled.

29. The balloon catheter system of claim 3 wherein the balloon includes an inner cylindrical surface and wherein inflation of the balloon secures the hollow member within the inner cylindrical surface of the balloon, the outer surface of the hollow member engaging the inner cylindrical surface of the balloon to restrict an inward radial expansion of the inner cylindrical surface so as to direct an outward radial expansion of an outer surface of the balloon.

30. The balloon catheter system of claim 29 wherein the inner surface of the hollow member defines the opening, and wherein the opening remains open during inflation of the balloon to permit blood to flow past the balloon for as long as the balloon remains inflated within an artery.

31. An adaptor for modifying a performance of an inflatable, balloon of an intravascular balloon catheter, the adaptor comprising:
a hollow member having a proximal end, a distal end, an outer surface, an inner surface and an opening between the proximal and distal ends; and
positioning means connected to the hollow member, for longitudinally moving the hollow member within a blood vessel, between a wall of the blood vessel and the catheter, and for positioning the hollow member so as to contact a surface of the balloon and effect the modified performance of the balloon.

32. The adaptor of claim 31 wherein the opening has a length of at least 10 millimeters.

33. The adaptor of claim 32 wherein the positioning means is made of a shape memory metal alloy.

34. The adaptor of claim 33 wherein the hollow member is noncompliant in a radial direction.

35. The adaptor of claim 34 wherein the opening of the hollow member is defined by the inner surface of the hollow member.

36. The adaptor of claim 35 wherein the hollow member is made of polyethylene.

37. The adaptor of claim 35 wherein the hollow member is made of polyethylene terephthalate (PET).

38. The adaptor of claim 37 wherein the proximal end and the distal end of the hollow member are biased.

39. The adaptor of claim 36 wherein the hollow member further includes geometric support means for maintaining a radial size of the opening of the hollow member when a force is applied to the outer surface of the hollow member.

40. The adaptor of claim 36 wherein the outer surface and the inner surface of the hollow member define a wall of the hollow member, and wherein the wall includes exposure means for exposing the opening through the wall.

41. The adaptor of claim 40 wherein the exposure means comprises a plurality of holes which are circumferentially spaced about the outer surface of the hollow member.

42. The adaptor of claim 35 wherein the hollow member is comprised of a tubular coil of a flat member, and wherein the exposure means comprises spaces between adjacent coils of the hollow member.

43. The adaptor of claim 42 wherein the flat member comprises a length of a metal material.

44. The adaptor of claim 43 wherein the metal material is radiopaque.

45. The adaptor of claim 42 wherein the flat member comprises a length of a polymer material.

46. The adaptor of claim 35 wherein the hollow member is comprised of a tubular braid of wire-like members, and wherein the exposure means comprises gaps between intersections of the wire-like members.

47. The adaptor of claim 46 wherein the wire-like members comprise strands of a metal material.

48. The adaptor of claim 47 wherein the metal material is radiopaque.

49. The adaptor of claim 33 wherein the hollow member is made of a compliant material.

50. The adaptor of claim 49 wherein the opening is defined between the inner surface and the outer surface of the hollow member.

51. The adaptor of claim 49 wherein the compliant material is silicone.

52. A method of treating an affected region of a blood vessel, the method comprising:
inserting into the blood vessel a catheter comprising a shaft having a proximal end, a distal end and a balloon connected at the distal end of the shaft, the balloon communicating with an inflation lumen of the catheter shaft;
positioning the balloon adjacent the affected region of the blood vessel;
inserting within the blood vessel, between the shaft of the catheter and a wall of the blood vessel, a hollow member having a proximal end, a distal end, an opening between the proximal end and the distal end, and an elongated member attached to the hollow member for positioning the hollow member in contact with a surface of the balloon;

applying a longitudinal force to the elongated member to locate the hollow member within the blood vessel adjacent to the balloon; and inflating the balloon so as to apply a force to the wall of the blood vessel and a surface of the hollow member, the force securing the hollow member against the balloon so as to effect a performance not capable by the balloon alone.

53. The method of claim 52 wherein the step of positioning the balloon includes:

inflating the balloon so as to apply a force to the wall of the blood vessel; and deflating the balloon so as to reduce a radial size of the balloon.

54. The method of claim 52 wherein the step of applying the longitudinal force to the elongated member comprises:

positioning the proximal end and distal end of the hollow member near a proximal and a distal end of the balloon, respectively.

55. The method of claim 54 wherein the step of positioning further includes positioning the opening between the balloon and the wall of the blood vessel.

56. The method of claim 55 wherein the step of inflating the balloon causes the opening of the hollow member to create a void past the inflated balloon which allows a flow of blood past the inflated balloon.

57. The method of claim 55 wherein the step of inflating the balloon causes an outer surface of the balloon to contact an inner surface of the hollow member, a radial size of the balloon therefore being restricted to a radial size of the hollow member.

58. A method of modifying an inflatable balloon of a dilatation balloon catheter, the method comprising:

inserting into the blood vessel a catheter comprising a shaft having a proximal end, a distal end and an inflatable balloon connected at the distal end of the shaft, the balloon communicating with an inflation lumen of the catheter shaft;

positioning the balloon adjacent the affected region of the blood vessel;

inserting within the blood vessel, between the shaft of the catheter and a wall of the blood vessel, a hollow member having a proximal end, a distal end, and an elongated member attached to the hollow member for positioning the hollow member in contact with a surface of the balloon;

applying a longitudinal force to the elongated member to locate the hollow member within the blood vessel adjacent to the balloon, with the proximal end and the distal end of the hollow member exposed past a proximal end and a distal end of the balloon; and inflating the balloon so as to cause at least part of the surface of the balloon to exert a force on a surface of the hollow member, the force securing the surface of the hollow member against the surface of the balloon such that the hollow member establishes a fluid pathway past the inflated balloon.

59. A method of modifying an inflatable balloon of a dilatation balloon catheter, the method comprising:

inserting into the blood vessel a catheter comprising a shaft having a proximal end, a distal end and a compliant, inflatable balloon connected at the distal end of the shaft, the balloon communicating with an inflation lumen of the catheter shaft;

positioning the balloon adjacent the affected region of the blood vessel;

inserting within the blood vessel, between the shaft of the catheter and a wall of the blood vessel, a hollow member having a proximal end, a distal end, an outer surface, an inner surface, the outer surface defining a predetermined diameter of the hollow member along at least a portion of the hollow member and an elongated member attached to the hollow member for positioning the hollow member in contact with a surface of the balloon;

applying a longitudinal force to the elongated member to position the inner surface of the hollow member over the balloon, with the proximal end and the distal end of the hollow member generally aligned with a proximal end and a distal end of the balloon; and inflating the balloon so as to cause an outer surface of the balloon to expand within the hollow member, the hollow member restricting a radial size of the balloon to the predetermined diameter of the hollow member and increasing an inflation pressure tolerance of the balloon.

* * * * *